(12) United States Patent
Cruse

(10) Patent No.: US 6,359,046 B1
(45) Date of Patent: Mar. 19, 2002

(54) HYDROCARBON CORE POLYSULFIDE SILANE COUPLING AGENTS FOR FILLED ELASTOMER COMPOSITIONS

(75) Inventor: Richard W. Cruse, Yorktown Heights, NY (US)

(73) Assignee: Crompton Corporation, Middlebury, CT (US)

(*) Notice: Subject to any disclaimer, the term of this patent is extended or adjusted under 35 U.S.C. 154(b) by 0 days.

(21) Appl. No.: 09/657,934

(22) Filed: Sep. 8, 2000

(51) Int. Cl.$^7$ .................................................. C08K 3/34
(52) U.S. Cl. ................... 524/262; 556/427; 556/482; 568/21; 568/61; 524/493; 524/424; 524/419; 524/261; 523/213
(58) Field of Search ............................ 556/427, 482; 568/21, 61; 524/493, 424, 419, 261, 262; 523/213

(56) References Cited

U.S. PATENT DOCUMENTS

| | | | |
|---|---|---|---|
| 3,476,826 A | * | 11/1969 | Millen |
| 3,842,111 A | | 10/1974 | Meyer-Simon et al. |
| 3,873,489 A | | 3/1975 | Thurn et al. |
| 3,946,059 A | | 3/1976 | Janssen et al. |
| 3,957,718 A | | 5/1976 | Pochert et al. |
| 3,978,103 A | | 8/1976 | Meyer-Simon et al. |
| 3,997,356 A | | 12/1976 | Thurn et al. |
| 3,997,581 A | | 12/1976 | Pletka et al. |
| 4,072,701 A | | 2/1978 | Pletka et al. |
| 4,076,550 A | | 2/1978 | Thurn et al. |
| 4,125,552 A | | 11/1978 | Speier |
| 4,128,438 A | | 12/1978 | Wolff et al. |
| 4,129,585 A | | 12/1978 | Buder et al. |
| 4,222,915 A | | 9/1980 | Wolff et al. |
| 4,229,333 A | | 10/1980 | Wolff et al. |
| 4,375,988 A | | 3/1983 | Mueller et al. |
| 4,384,132 A | | 5/1983 | Schwarz et al. |
| 4,408,064 A | | 10/1983 | Schwarz et al. |
| 4,444,936 A | | 4/1984 | Schwarz et al. |
| 4,507,490 A | | 3/1985 | Panster et al. |
| 4,514,231 A | | 4/1985 | Kerner et al. |
| 4,517,336 A | | 5/1985 | Wolff et al. |
| 4,524,169 A | | 6/1985 | Wolff et al. |
| 4,704,414 A | | 11/1987 | Kerner et al. |
| 4,820,751 A | | 4/1989 | Takeshita et al. |
| 4,992,098 A | | 2/1991 | Lotze et al. |
| 5,037,872 A | | 8/1991 | Schwarze et al. |
| 5,116,886 A | | 5/1992 | Wolff et al. |
| 5,159,009 A | | 10/1992 | Wolff et al. |
| 5,399,739 A | | 3/1995 | French et al. |

(List continued on next page.)

FOREIGN PATENT DOCUMENTS

| | | |
|---|---|---|
| AU | A5034996 | 10/1996 |
| AU | A1008297 | 7/1997 |
| CA | 2146333 | 4/1994 |
| CA | 2148333 | 11/1995 |
| CA | 2231302 | 9/1998 |
| CA | 2270502 A1 | 10/1999 |
| DE | 2141160 | 3/1973 |
| DE | 4236218 A1 | 6/1993 |
| DE | 4308311 C2 | 4/1995 |
| DE | 19702046 A1 | 1/1998 |
| EP | 0631982 A3 | 1/1995 |
| EP | 0631982 A2 | 1/1995 |
| EP | 764687 A1 | 8/1996 |
| EP | 732362 A1 | 9/1996 |
| EP | 784072 A1 | 7/1997 |
| EP | 795577 A1 | 9/1997 |
| EP | 864605 A2 | 9/1998 |
| EP | 864605 A3 | 9/1998 |
| EP | 732362 B1 | 6/1999 |
| EP | 919559 A2 | 6/1999 |
| EP | 919559 A3 | 9/1999 |
| GB | 2259303 A | 3/1993 |
| WO | WO98/53004 | 11/1998 |
| WO | WO00/05300 | 2/2000 |

OTHER PUBLICATIONS

ASTM No. 224–89. "Standard Specification for Smooth–Surfaced Asphalt Roll Roofing (Organic Felt)" Copyright by the American Society for Testing Materials. (1989).
ASTM No. D–2084–95 "Standard Test Method for Rubber Property–Vulcanization Using Oscillating Disk Cure Meter" Copyright by the American Society for Testing Materials. (1995).
ASTM No. D–3849–95a "Standard Test Method for Carbon Black—Primary Aggregate Dimensions from Electron Microscope Image Analysis" (1995).
ASTM No. D–2240–97 Standard Test Method for Rubber Property—Durometer Hardness (1997).
ASTM No. D–412–98a. "Standard Test Methods for Vulcanized Rubber and Thermoplastic Elastomers—Tension" (1998).
ASTM No. D–623–99. Standard Test Methods for Rubber Property—Heat Generation and Flexing Fatigue in Compression (1999).
ASTM No. D–1646–99 Standard Test Methods for Rubber—Viscosity, Stress Relaxation, and Pre–Vulcanization Characteristics (Mooney Viscometer) (1999).

(List continued on next page.)

*Primary Examiner*—Robert Dawson
*Assistant Examiner*—Kuo-Liang Peng
(74) *Attorney, Agent, or Firm*—Michael P. Dilworth

(57) ABSTRACT

The present invention discloses novel hydrocarbon core polysulfide silanes and methods of preparing the hydrocarbon core polysulfide silanes. Preferably, the silanes of the present invention contain assemblies of a single unit of a hydrolyzable silane group, tethered to one end of a chain of sulfur atoms, and several of these assemblies are bound to a common central hydrophobic core via the other end of the sulfur atoms chain. The hydrocarbon core polysulfide silanes may be incorporated into filled elastomeric compositions providing improved dispersiblity of the filler materials. Mineral fillers may be pre-treated with the hydrocarbon core polysulfide silanes prior to use in elastomeric compositions.

41 Claims, No Drawings

U.S. PATENT DOCUMENTS

| | | |
|---|---|---|
| 5,401,789 A | 3/1995 | Wolff et al. |
| 5,405,985 A | 4/1995 | Parker et al. |
| 5,466,767 A | 11/1995 | Wieland et al. |
| 5,468,893 A | 11/1995 | Parker et al. |
| 5,605,951 A | 2/1997 | Sandstrom et al. |
| 5,650,457 A | 7/1997 | Scholl et al. |
| 5,663,358 A | 9/1997 | Cohen et al. |
| 5,663,395 A | 9/1997 | Göbel et al. |
| 5,663,396 A | 9/1997 | Musleve et al. |
| 5,672,639 A | 9/1997 | Corvasce et al. |
| 5,674,932 A | 10/1997 | Agostini et al. |
| 5,675,014 A | 10/1997 | Cohen et al. |
| 5,679,728 A | 10/1997 | Kawazura et al. |
| 5,684,172 A | 11/1997 | Wideman et al. |
| 5,698,619 A | 12/1997 | Cohen et al. |
| 5,719,207 A | 2/1998 | Cohen et al. |
| 5,723,529 A | 3/1998 | Bernard et al. |
| 5,728,778 A | 3/1998 | D'Sidocky et al. |
| 5,733,963 A | 3/1998 | Sandstrom et al. |
| 5,753,732 A | 5/1998 | Wideman et al. |
| 5,770,754 A | 6/1998 | Scholl |
| 5,789,080 A | 8/1998 | Grimberg et al. |
| 5,817,852 A | 10/1998 | Ichinohe et al. |
| 5,859,275 A | 1/1999 | Münzenberg et al. |
| 5,958,161 A | 9/1999 | Grimberg et al. |
| 5,977,225 A | 11/1999 | Scholl et al. |
| 5,989,712 A | 11/1999 | Grimberg et al. |

OTHER PUBLICATIONS

K. Garde, W.J. McGill and C.D. Woolard: "Surface Modification of Fly Ash—Characterization and Evaluation as Reinforcing Filler in Polyisoprene" appearing in *Plastics, Rubber and Compositions*, No. 1, vol. 28. At p. 1–10 (1999).

The Vanderbilt Rubber Handbook. Thirteenth Edition (1990) pp. 344–347.

Bayer Manual for the Rubber Industry. $2^{nd}$ fully revised edition (1993) "Foreword".

* cited by examiner

HYDROCARBON CORE POLYSULFIDE SILANE COUPLING AGENTS FOR FILLED ELASTOMER COMPOSITIONS

BACKGROUND OF THE INVENTION

1. Field of the Invention

This invention relates to compositions comprising novel polysulfide-silane coupling agents, referred to as hydrocarbon core polysulfide silanes, rubber compositions incorporating the novel polysulfide silanes, and methods of preparing the same. The hydrocarbon core polysulfide silanes of the present invention may be used in coupling mineral fillers within elastomeric compositions, particularly rubber, wherein specific characteristics of the polysulfide silanes may be tailored towards specific characteristics of the elastomeric composition.

2. Description of Related Art

Typically, sulfur-containing coupling agents for mineral-filled elastomers involve silanes in which two alkoxysilyl groups are bound, each to one end of a chain of sulfur atoms. The chemical bond in these molecules between the two silicon atoms and sulfur is indirect, being mediated by two similar and, in most cases, identical hydrocarbon fragments. This general silane structure almost invariably relies on a chain of three methylene groups as the two mediating hydrocarbon units, and upon the use of two triethoxysilyl groups. In the most notable exceptions, the methylene chain is shorter, containing only one or two methylenes per chain.

The prior art discloses the composition, preparation, and use of these coupling agents in a number of applications, but primarily as coupling agents for mineral-filled elastomers. These coupling agents function by chemically bonding silica or other mineral fillers to polymer when used in rubber applications. Coupling is accomplished by chemical bond formation between the silane sulfur and the polymer and by hydrolysis of the silane alkoxy groups and subsequent condensation with silica hydroxyl groups.

Canadian Patent Application No. 2,231,302 to Scholl et al. (Scholl et al. '302) discloses rubber mixtures containing at least one rubber, a filler, optional rubber auxiliaries and at least one polysulphide polyether silane having the formula $$R^1R^2R^3Si-X^1-(-S_x\text{-polyether}-)_m-(-S_x-X^2-SiR^1R^2R^3)_n$$

for use in preparing rubber vulcanisates from which are produced low rolling resistance tires having good wet skid resistance and a high abrasion resistance. The rubber mixtures disclosed contain from 0.1 to 10 wt. % of the polysulphide polyether silane. When a mixture of oligomers of the polysulphide polyether silanes are used, the average molecular weight is about 800 to 10,000.

In the case of Scholl et al. '302, the polyether portions of the molecules, upon standing, may form peroxides which cause degradation of the resultant rubber compositions. Furthermore, the polyether portions of the silane compete with other rubber constituents.

Thus, it would be advantageous to provide a novel polysulfide composition having more than two silyl groups without the necessity of ether linkages for enhanced performance in filled elastomer compositions, rubber compositions, and use in tire compositions.

Bearing in mind the problems and deficiencies of the prior art, it is therefore an object of the present invention to provide a novel polysulfide silane composition having more than two silyl groups and a method of making the same.

It is another object of the present invention to provide a non-collinear polysulfide silane composition to provide enhanced dispersibility of the filler within an elastomeric composition, rubber compositions, and tire compositions and a method of making the same.

A further object of the invention is to provide a filled elastomeric composition, rubber composition and tire compositions containing a polysulfide silane having improved filler dispersion.

It is yet another object of the present invention to provide a low rolling resistance tire having enhanced performance.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a polysulfide silane composition having the formula:

$$(X^1X^2X^3Si-J-S_x-)_p-G$$

wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom of R, and G is a hydrocarbon fragment obtained by removal of a p quantity of hydrogen atoms of a hydrocarbon having from 1 to 30 carbon atoms.

Preferably, $X^1$, $X^2$ and $X^3$ are the same hydrolyzable functionalities with ethoxy being most preferred. Alternatively, $X^1$, $X^2$ and $X^3$ may also each be different hydrolyzable functionalities. Preferably, p is 3 to 6; x is 2 to 8; R is a hydrocarbon functionality selected from the group consisting of straight chain alkyl, alkenyl, aryl and aralkyl groups; and J is selected from the group consisting of methylene, ethylene, propylene, isobutylene, and diradicals obtained by loss of hydrogen atoms at a 2,4 or 2,5 position of norbornane, an alpha position of 2-norbornylethane, a beta position of 2-norbornylethane, a 4 position of 2-norbornylethane, or a 5 position of 2-norbornylethane.

When p is 3 and G is preferably glyceryl. Alternatively, G may be a hydrocarbon fragment obtained by removal of 3 hydrogen atoms from 2-norbornylethane. G may also be a hydrocarbon fragment obtained by removal of 3 hydroxyl groups from a trimethylolalkane. When p is 4 and G is preferably pentaerythrityl. Alternatively, G may be a hydrocarbon fragment obtained by removal of 4 hydrogen atoms from 2-norbornylethane. When p is greater than 4 and G may be a hydrocarbon fragment obtained by removal of more then 4 hydrogen atoms from a hydrocarbon selected from the group consisting of cyclododecane, triethylcyclohexane, 2,6-dimethyloctane, and squalane. G may also contain a tertiary amine functionality or a cyano functionality.

In a second aspect, the present invention is directed to a polysulfide silane composition comprising one or more isomers of tetrakis-1,3,4,5-(3-triethoxysilyl-1-propyltetrathio)neopentane.

In a third aspect, the present invention is directed to a polysulfide silane composition comprising one or more isomers of tris-1,2,3-(3-triethoxysilyl-1-propyltetrathio)propane.

In a fourth aspect, the present invention is directed to a process of making a hydrocarbon core polysulfide silane having the formula $$(X^1X^2X^3Si-J-S_x-)_p-G$$

wherein p is 3 to 12, x is 2 to 20, $X^1$ is a hydrolyzable functionality selected from the group consisting of —Cl, —Br, —OH, —O—N=C(R)$_2$, —OR, or RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom of R, and G is a hydrocarbon fragment obtained by removal of a p quantity of hydrogen atoms of a hydrocarbon having from 1 to 30 carbon atoms, comprising the steps of: providing a mercaptan; deprotonating the mercaptan; providing a source of elemental sulfur; forming a reactive sulfur anion by reacting the deprotonated mercaptan with the elemental sulfur; and coupling the reactive sulfur anion with a carbon containing substrate.

Preferably, the step of providing the mercaptan comprises providing a mercaptan having a formula $X^1X^2X^3Si$—J—SH wherein the mercaptan is most preferably selected from the group consisting of 3-mercapto-1-propyltriethoxysilane and 3-mercapto-1-propylmethyldiethoxysilane.

Alternatively, the step of providing the mercaptan comprises providing a mercaptan having a formula $(HS_x-)_pG$ wherein the mearcaptan is most preferably selected from the group consisting of 2,2-bis(mercaptomethyl)-1,3-dimercaptopropane and 1,2,3-trimercaptopropane.

The step of deprotonating the mercaptan may comprise deprotonating the mercaptan with a Brönsted base using p equivalents of the base for each mole of mercaptan or with an amine type base.

Most preferably, the step of forming the reactive sulfur anion is sufficiently complete prior to introduction of the carbon containing substrate.

In a fifth aspect, the present invention is directed to an elastomeric composition comprising at least one hydrocarbon core polysulfide silane having the formula:

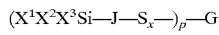

wherein p is 3 to 12, x is 2 to 20, $X^1$ is a hydrolyzable functionality selected from the group consisting of —Cl, —Br, —OH, —O—N=C(R)$_2$, —OR, or RC(=O)O—, in which R is a hydrocarbon fragment obtained by removing one hydrogen atom from a hydrocarbon having 1 to 20 carbon atoms, $X^2$ and $X^3$ are $X^1$, R or hydrogen, J is a hydrocarbon fragment obtained by removal of one hydrogen atom of R, and G is a hydrocarbon fragment obtained by removal of a p quantity of hydrogen atoms of a hydrocarbon having from 1 to 30 carbon atoms; an unsaturated organic polymer; and a filler.

Preferably, the at least one hydrocarbon core polysulfide silane is one or more isomers of tetrakis-1,3,4,5-(3-triethoxysilyl-1-propyltetrathio)neopentane or tris-1,2,3-(3-triethoxysilyl-1-propyltetrathio)propane. Most preferably, the at least one hydrocarbon core polysulfide silane is present in an amount of about 0.05 to about 25 phr.

The elastomeric composition preferably comprises a filler present in an amount of about 1 to about 85 wt. % carbon black based on a total weight of the filler and at least one hydrocarbon core polysulfide silane is present in an amount of about 0.1 to about 20 wt. % of the hydrocarbon core polysulfide silane based on a total weight of the filler.

In a sixth aspect, the present invention is directed to a method of making a rubber composition comprising the steps of providing at least one isomer of a hydrocarbon core polysulfide silane having the formula

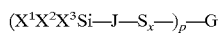

wherein p is 3 to 12, x is 2 to 20, p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom of R, and G is a hydrocarbon fragment obtained by removal of a p quantity of hydrogen atoms of a hydrocarbon having from 1 to 30 carbon atoms; providing an organic polymer; providing a filler; thermomechanically mixing the organic polymer, filler and hydrocarbon core polysulfide silane to form a rubber mixture; curing the rubber mixture to form a rubber composition having enhanced dispersion of the filler.

Preferably, during the step of providing the filler, the filler has been pretreated with all or a portion of the at least one isomer of the hydrocarbon core polysulfide silane.

The process may further include the step of adding curing agents to the rubber mixture in another thermomechanical mixing stage.

Preferably, the hydrocarbon core polysulfide silane is one or more isomers of tetrakis-1,3,4,5-(3-triethoxysilyl-1-propyltetrathio)neopentane or one or more isomers of tris-1,2,3-(3-triethoxysilyl-1-propyltetrathio)propane.

In a seventh aspect, the present invention is directed to a filler for dispersion in elastomeric compositions comprising: mineral particulates; and at least one hydrocarbon core polysulfide silane having the formula:

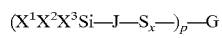

wherein p is 3 to 12, x is 2 to 20, $X^1$ is a hydrolyzable functionality selected from the group consisting of —Cl, —Br, —OH, —O—N=C(R)$_2$, —OR, or RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom of R, and G is a hydrocarbon fragment obtained by removal of a p quantity of hydrogen atoms of a hydrocarbon having from 1 to 30 carbon atoms.

Preferably, the mineral particulates are siliceous particulates. The filler of this aspect may further comprise carbon black. Preferably, the at least one hydrocarbon core polysulfide silane is one or more isomers of tetrakis-1,3,4,5-(3-triethoxysilyl-1-propyltetrathio)neopentane or one or more isomers of tris-1,2,3-(3-triethoxysilyl-1-propyltetrathio)propane.

DESCRIPTION OF THE PREFERRED EMBODIMENT(S)

The present invention discloses novel hydrocarbon core polysulfide silanes which exhibit advantages as coupling agents for mineral-filled elastomers over prior art polysulfide silanes. The polysulfide silanes are advantageous over the prior art in that they have tailored characteristics to enhance their performance as a result of specific molecular structures. The present invention further relates to the method of preparing the novel hydrocarbon core polysulfide silanes, the novel elastomeric compositions, and a filler treated with the novel hydrocarbon core polysulfide silanes.

As used herein, "alkyl" includes straight, branched and cyclic alkyl groups, "alkenyl" includes straight, branched and cyclic alkenyl groups containing one or more carbon-carbon double bonds, "alkynyl" includes straight, branched, and cyclic alkynyl groups containing one or more carbon-carbon triple bonds and optionally also one or more carbon-carbon double bonds as well, "aryl" includes aromatic hydrocarbons, and "aralkyl" includes aliphatically substituted aromatic hydrocarbons. Specific alkyls include methyl, ethyl, propyl, isobutyl, specific aryls include phenyl, and specific aralkyls include tolyl and phenethyl. As used herein, "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples of the aforementioned cyclic structures include norbornyl, norbornenyl, ethylnorbornyl, ethylnorbornenyl, ethylcyclohexyl, ethylcyclohexenyl, cyclohexylcyclohexyl, and cyclododecatrienyl.

The hydrocarbon core polysulfide silanes of the present invention are represented by the following general formula:

$$(X^1X^2X^3Si\text{—}J\text{—}S_x\text{—})_p\text{—}G \quad \text{(Formula I)}$$

wherein p is 3 to 12, x is 2 to 20, $X^1$ is selected from the group of hydrolyzable groups consisting of —Cl, —Br, —OH, —O—N=C(R)$_2$, —OR, or RC(=O)O—, in which R is any hydrocarbon fragment obtained by removing one hydrogen atom from a hydrocarbon having from 1 to 20 carbon atoms including branched or straight chain alkyl, alkenyl, aryl or aralkyl groups; $X^2$ and $X^3$ may be hydrogen, the members listed above for R, or the members listed above for $X^1$; J is preferably a hydrocarbon fragment obtained by removal of one hydrogen atom of any of the groups listed above for R; and G is a fragment obtained by removal of a quantity of hydrogen atoms given by p, of any hydrocarbon having from 1 to 30 carbon atoms.

G includes, but is not limited to, branched, straight-chain, cyclic, and/or polycyclic aliphatic hydrocarbon fragments. Alternatively, G may contain a tertiary amine functionality via nitrogen atoms each bound to three separate carbon atoms and/or cyano (CN) groups; aromatic hydrocarbons; and arenes derived by substitution of the aforementioned aromatics with branched or straight chain alkyl, alkenyl, alkynyl, aryl and/or aralkyl groups.

Representative examples of $X^1$ include methoxy, ethoxy, propoxy, isopropoxy, butoxy, phenoxy, benzyloxy, hydroxy, chloro, and acetoxy. Methoxy, ethoxy, and isopropoxy are preferred. Ethoxy is most preferred. Representative examples of $X^1$ and $X^3$ include the representative examples listed above for $X^1$ as well as hydrogen, methyl, ethyl, propyl, isopropyl, sec-butyl, phenyl, vinyl, cyclohexyl, and higher straight-chain alkyl, such as butyl, hexyl, octyl, lauryl, and octadecyl. Methoxy, ethoxy, isopropoxy, methyl, ethyl, phenyl, and the higher straight-chain alkyls are preferred for $X^2$ and $X^3$. Ethoxy, methyl and phenyl are most preferred. In a most preferred embodiment, $X^1$, $X^2$ and $X^3$ are the same alkoxy groups with ethoxy being most ideal.

Representative examples of J include the terminal straight-chain alkyls further substituted terminally at the other end, such as —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their beta-substituted analogs, such as —CH$_2$(CH$_2$)$_m$CH(CH$_3$)—, where m is zero to 17; —CH$_2$CH$_2$C(CH$_3$)$_2$CH$_2$—; the structure derivable from methallyl chloride, —CH$_2$CH (CH$_3$)CH$_2$—; any of the structures derivable from divinylbenzene, such as —CH$_2$CH$_2$(C$_6$H$_4$)CH$_2$CH$_2$— and —CH$_2$CH$_2$(C$_6$H$_4$)CH(CH$_3$)—, where the notation C$_6$H$_4$ denotes a disubstituted benzene ring; any of the structures derivable from butadiene, such as —CH$_2$CH$_2$CH$_2$CH$_2$—, —CH$_2$CH$_2$CH(CH$_3$)—, and —CH$_2$CH(CH$_2$CH$_3$)—; any of the structures derivable from piperylene, such as —CH$_2$CH$_2$CH$_2$CH(CH$_3$)—, —CH$_2$CH$_2$CH(CH$_2$CH$_3$)—, and —CH$_2$CH(CH$_2$CH$_2$CH$_3$)—; any of the structures derivable from isoprene, such as —CH$_2$CH(CH$_3$)CH$_2$CH$_2$—, —CH$_2$CH(CH$_3$)CH(CH$_3$)—, —CH$_2$C(CH$_3$)(CH$_2$CH$_3$)—, —CH$_2$CH$_2$CH(CH$_3$)CH$_2$—, —CH$_2$CH$_2$C(CH$_3$)$_2$— and —CH$_2$CH[CH(CH$_3$)$_2$]—; any of the isomers of —CH$_2$CH$_2$-norbornyl—, —CH$_2$CH$_2$-cyclohexyl—; any of the diradicals obtainable from norbornane, cyclohexane, cyclopentane, tetrahydrodicyclopentadiene, or cyclododecene by loss of two hydrogen atoms; the structures derivable from limonene, —CH$_2$CH(4-methyl-1-C$_6$H$_9$-)CH$_3$, where the notation C$_6$H$_9$ denotes isomers of the trisubstituted cyclohexane ring lacking substitution in the 2 position; any of the monovinyl-containing structures derivable from trivinylcyclohexane, such as —CH$_2$CH$_2$(vinylC$_6$H$_9$)CH$_2$CH$_2$— and —CH$_2$CH$_2$(vinylC$_6$H$_9$)CH (CH$_3$)—, where the notation C$_6$H$_9$ denotes any isomer of the trisubstituted cyclohexane ring; any of the monounsaturated structures derivable from myrcene containing a trisubstituted C=C, such as —CH$_2$CH[CH$_2$CH$_2$CH=C(CH$_3$)$_2$]CH$_2$CH$_2$—, —CH$_2$CH[CH$_2$CH$_2$CH=C(CH$_3$)$_2$]CH(CH$_3$)—, —CH$_2$C[CH$_2$CH$_2$CH=C(CH$_3$)$_2$](CH$_2$CH$_3$)—, —CH$_2$CH$_2$CH[CH$_2$CH$_2$CH=C(CH$_3$)$_2$]CH$_2$—, —CH$_2$CH$_2$(C—)(CH$_3$)[CH$_2$CH$_2$CH=C(CH$_3$)$_2$], and —CH$_2$CH{CH (CH$_3$)[CH$_2$CH$_2$CH=C(CH$_3$)$_2$]}—; and any of the monounsaturated structures derivable from myrcene lacking a trisubstituted C=C, such as —CH$_2$CH(CH=CH2)CH$_2$CH$_2$CH$_2$C(CH$_3$)$_2$—, —CH$_2$CH(CH=CH$_2$)CH$_2$CH$_2$CH[CH(CH$_3$)$_2$]—, —CH$_2$C(=CH—CH$_3$)CH$_2$CH$_2$CH$_2$C(CH$_3$)$_2$—, —CH$_2$C(=CH—CH$_3$)CH$_2$CH$_2$CH[CH(CH$_3$)$_2$]—, —CH$_2$CH$_2$C(=CH$_2$)CH$_2$CH$_2$CH$_2$C(CH$_3$)$_2$—, —CH$_2$CH$_2$C(=CH$_2$)CH$_2$CH$_2$CH[CH(CH$_3$)$_2$]—, —CH$_2$CH=C(CH$_3$)$_2$CH$_2$CH$_2$CH$_2$C(CH$_3$)$_2$—, and —CH$_2$CH=C(CH$_3$)$_2$CH$_2$CH$_2$CH[CH(CH$_3$)$_2$]. The preferred structures for J are —CH$_2$—, —CH$_2$CH$_2$— —CH$_2$CH$_2$CH$_2$—, —CH$_2$CH(CH$_3$)CH$_2$—, and any of the diradicals obtained by 2,4 or 2,5 disubstitution of the norbornane-derived structures listed above. —CH$_2$CH$_2$CH$_2$— is most preferred.

Representative examples of tridentate G include any of the structures derivable from nonconjugated terminal diolefins, such as —CH$_2$(CH$_2$)$_{q+1}$CH(CH$_2$—)— and —CH(CH$_3$)(CH$_2$)$_q$CH(CH$_2$—)—, in which q is zero to 20; any of the structures derivable from divinylbenzene, such as —CH$_2$CH$_2$(C$_6$H$_4$)CH(CH$_2$—)— and —CH(CH$_3$)(C$_6$H$_4$) CH(CH$_2$—)—, where the notation C$_6$H$_4$ denotes a disubstituted benzene ring; any of the structures derivable from butadiene, such as —CH$_2$(CH—)CH$_2$CH$_2$— and —CH (CH$_3$)CH—(CH$_2$—)—; any of the structures derivable from piperylene, such as —CH$_2$(CH—)(CH—)CH$_2$CH$_3$, —CH$_2$(CH—)CH$_2$CH(CH$_3$)—, —CH$_2$CH$_2$(CH—)CH(CH$_3$)—, and —CH$_2$(CH$_3$)(CH—)CH(CH$_3$)—; any of the structures derivable from isoprene, such as —CH$_2$(C—)(CH$_3$)CH (CH$_3$)—, —CH$_2$(C—)(CH$_3$)CH$_2$CH$_2$—, —CH$_2$CH(CH$_3$) (CH—)CH$_2$—, and —C(CH$_3$)$_2$(CH—)CH$_2$—; any of the structures derivable from vinylnorbornene and vinylcyclohexene, such as —CH$_2$CH$_2$-norbornyl(-)$_2$, —CH (CH$_3$)-norbornyl(-)$_2$, —CH$_2$(CH—)-norbornyl—, —CH$_2$CH$_2$-cyclohexyl(-)$_2$, —CH(CH$_3$)-cyclohexyl(-)$_2$, and —CH$_2$(CH—)-cyclohexyl—; any of the structures derivable from limonene, such as —CH$_2$CH(CH$_3$)[4-methyl-1-C$_6$H$_8$(-)$_2$CH$_3$], —(CH$_3$)$_2$C[4-methyl-1-C$_6$H$_8$(-)$_2$CH$_3$], and —CH$_2$(C—)(CH$_3$)[(4-methyl-1—C$_6$H$_9$—)CH$_3$], where the notation C$_6$H$_9$ denotes isomers of the trisubstituted cyclohexane ring lacking substitution in the 2 position and where C$_6$H$_8$ denotes the 1,4 disubstituted cyclohexene ring; any of the vinyl-containing structures derivable from trivinylcyclohexane, such as —CH$_2$(CH—)(vinylC$_6$H$_9$)CH$_2$CH$_2$— and —CH$_2$(CH—)(vinylC$_6$H$_9$)CH(CH$_3$)—; any of the saturated structures derivable from trivinylcyclohexane, such as (—CH$_2$CH$_2$)$_3$C$_6$H$_9$, (—CH$_2$CH$_2$)$_2$C$_6$H$_9$CH(CH$_3$)—, —CH$_2$CH$_2$C$_6$H$_9$[CH(CH$_3$)—]$_2$, and C$_6$H$_9$[CH(CH$_3$)—]$_3$, -where the notation C$_6$H$_9$ denotes any isomer of the trisubstituted cyclohexane ring; any structure derivable by trisubstitution of cyclopentane, tetrahydrocyclopentadiene, cyclododecane, or any of the cyclododecenes; any of the monounsaturated structures derivable from myrcene in which this structure contains a trisubstituted C=C, such as —CH$_2$(C—)[CH$_2$CH$_2$CH=C(CH$_3$)$_2$]CH(CH$_3$)—, —CH$_2$(C—)[CH$_2$CH$_2$CH=C(CH$_3$)$_2$]CH$_2$CH$_2$—, —CH$_2$CH[CH$_2$CH$_2$CH=C(CH$_3$)$_2$](CH—)CH$_2$—, and —C(CH$_3$)[CH$_2$CH$_2$CH=C(CH$_3$)$_2$](CH—)CH$_2$—; any of the monounsaturated structures derivable from myrcene in which these structures lack a trisubstituted C=C, such as —CH$_2$CH(CH=CH$_2$)CH$_2$CH$_2$(CH—)C(CH$_3$)$_2$—, —C(CH$_3$)(CH=CH$_2$)CH$_2$CH$_2$(CH—)C(CH$_3$)$_2$—, —CH(CH$_3$)C(=CH$_2$)CH$_2$CH$_2$(CH—)C(CH$_3$)$_2$—, —CH$_2$CH$_2$C(=CH$_2$)CH$_2$CH$_2$(CH—)C(CH$_3$)$_2$—, —CH$_2$C(=CHCH$_3$)CH$_2$CH$_2$(CH—)C(CH$_3$)$_2$—, —CH$_2$CH=C(CH$_3$)CH$_2$CH$_2$(CH—)C(CH$_3$—, —CH$_2$(C—)(C$_2$H$_5$)CH$_2$CH$_2$(CH—)CH(CH$_3$)$_2$, —CH$_2$(C—)(C$_2$H$_5$)CH$_2$CH$_2$CH$_2$C(CH$_3$)$_2$—, —CH$_2$(CH—)CH(CH$_3$)CH$_2$CH$_2$(CH—)CH(CH$_3$)$_2$, —CH$_2$(CH—)CH(CH$_3$)CH$_2$CH$_2$CH$_2$C(CH$_3$)$_2$—, —CH$_2$CH(CH$_2$CH$_2$—)CH$_2$CH$_2$(CH—)CH(CH$_3$)$_2$, —CH$_2$CH(CH$_2$CH$_2$—)CH$_2$CH$_2$CH$_2$C(CH$_3$)$_2$— and cyclo-C$_{12}$H$_{15}$(-)$_3$; any of the saturated structures derivable from myrcene, such as —CH$_2$CH(—CHCH$_3$)CH$_2$CH$_2$(CH—)CH(CH$_3$)$_2$, —CH$_2$CH(—CHCH$_3$)CH$_2$CH$_2$CH$_2$C(CH$_3$)$_2$—, —CH$_2$CH(CH$_2$CH$_2$—)CH$_2$CH$_2$(CH—)CH(CH$_3$)$_2$, —CH$_2$CH(CH$_2$CH$_2$—)CH$_2$CH$_2$CH$_2$C(CH$_3$)$_2$—, —C(CH$_3$)(—CHCH$_3$)CH$_2$CH$_2$(CH—)CH(CH$_3$)$_2$, —C(CH$_3$)(—CHCH$_3$)CH$_2$CH$_2$CH$_2$C(CH$_3$)$_2$—, —C(CH$_3$)(CH$_2$CH$_2$—)CH$_2$CH$_2$(CH—)CH(CH$_3$)$_2$, and —C(CH$_3$)(CH$_2$CH$_2$—)CH$_2$CH$_2$CH$_2$C(CH$_3$)$_2$—; the structures derivable from trimethylolalkanes, such as CH$_3$CH$_2$CH$_2$C(CH$_2$—)$_3$ and CH$_3$CH$_2$C(CH$_2$—)$_3$; glyceryl, whose structure is —CH$_2$(CH—)CH$_2$—, and its methyl analog, whose structure is —CH$_2$(—CCH$_3$)CH$_2$—; and the triethanolamine derivative, (—CH$_2$CH$_2$)$_3$N.

The preferred structures of tridentate G include any of the structures derivable from vinylnorbornene and vinylcyclohexene, such as —CH$_2$CH$_2$-norbornyl(-)$_2$, —CH(CH$_3$)-norbornyl(-)$_2$, —CH$_2$(CH—)-norbornyl—, —CH$_2$CH$_2$-cyclohexyl(-)$_2$, —CH(CH$_3$)-cyclohexyl(-)$_2$, and —CH$_2$(CH—)-cyclohexyl—; any of the saturated structures derivable from trivinylcyclohexane, such as (—CH$_2$CH$_2$)$_3$C$_6$H$_9$, (—CH$_2$CH$_2$)$_2$C$_6$H$_9$CH(CH$_3$)—, —CH$_2$CH$_2$C$_6$H$_9$[CH(CH$_3$)—]$_2$, and C$_6$H$_9$[CH(CH$_3$)—]$_3$, where the notation C$_6$H$_9$ denotes any isomer of the trisubstituted cyclohexane ring; any of the trisubstituted cyclododecane structures; any of the saturated structures derivable from myrcene, such as —CH$_2$CH(—CHCH$_3$)CH$_2$CH$_2$(CH—)CH(CH$_3$)$_2$, —CH$_2$CH(-CHCH$_3$)CH$_2$CH$_2$CH$_2$C(CH$_3$)$_2$—, —CH$_2$CH(CH$_2$CH$_2$—)CH$_2$CH$_2$(CH—)CH(CH$_3$)$_2$, —CH$_2$CH(CH$_2$CH$_2$—)CH$_2$CH$_2$CH$_2$C(CH$_3$)$_2$—, —C(CH$_3$)(—CHCH$_3$)CH$_2$CH$_2$(CH—)CH(CH$_3$)$_2$,—C(CH$_3$(—CHCH$_3$)CH$_2$CH$_2$CH$_2$C(CH$_3$)$_2$—, —C(CH$_3$)(CH$_2$CH$_2$—)CH$_2$CH$_2$(CH—)CH(CH$_3$)$_2$, and —C(CH$_3$)(CH$_2$CH$_2$—)CH$_2$CH$_2$CH$_2$C(CH$_3$)$_2$—; the structures derivable from trimethylolalkanes, such as CH$_3$CH$_2$C(CH$_2$—)$_3$ and CH$_3$C(CH$_2$—)$_3$; and glyceryl, whose structure is —CH$_2$(CH—)CH$_2$—.

Most preferred are glyceryl; the structures derivable from trimethylolalkanes, such as CH$_3$CH$_2$C(CH$_2$—)$_3$ and CH$_3$C(CH$_2$—)$_3$; and any of the structures derivable from vinylnorbornene, such as —CH$_2$CH$_2$-norbornyl(-)$_2$, —CH(CH$_3$)-norbornyl(-)$_2$, and —CH$_2$(CH—)-norbornyl—.

Representative examples of tetradentate G include any of the structures derivable from nonconjugated terminal diolefins, such as —CH(CH$_2$)(CH$_2$)$_q$CH(CH$_2$—, in which q is from 1 to 20; any of the structures derivable from divinylbenzene, such as —CH$_2$(CH—)(C$_6$H$_4$)CH(CH$_2$—)—, where the notation C$_6$H$_4$ denotes a disubstituted benzene ring; any of the structures derivable from butadiene, such as —CH$_2$(CH—)(CH—)CH$_2$—; any of the structures derivable from piperylene, such as —CH$_2$(CH—)(CH—)CH$_2$(CH$_3$)—; any of the structures derivable from isoprene, such as —CH$_2$(C—)(CH$_3$)(CH—)CH$_2$—; any of the structures derivable from vinylnorbornene or vinylcyclohexene, such as —CH$_2$(CH—)-norbornyl(-)$_2$ and —CH$_2$(CH—)cyclohexyl(-)$_2$; any of the structures derivable from limonene, such —CH$_2$(C—)(CH$_3$)[4-methyl-1-C$_6$H$_8$(-)$_2$CH$_3$], where the notation C$_6$H$_8$ denotes the 1,4 disubstituted cyclohexene ring; any of the vinyl-containing structures derivable from trivinylcyclohexane, such as —CH$_2$(CH—)(vinylC$_6$H$_9$)(CH—)CH$_2$—, where the notation C$_6$H$_9$ denotes any isomer of the trisubstituted cyclohexane ring; any of the saturated structures derivable from trivinylcyclohexane, such as —CH$_2$(CH—)C$_6$H$_9$[CH(CH$_3$)—]$_2$, —CH$_2$(CH—)C$_6$H$_9$[CH$_2$CH$_2$—]$_2$, and —CH$_2$(CH—)C$_6$H$_9$[CH(CH$_3$)—][CH$_2$CH$_2$—], where the notation C$_6$H$_9$ denotes any isomer of the trisubstituted cyclohexane ring; any structure derivable by tetrasubstitution of cyclopentane, tetrahydrocyclopentadiene, cyclododecane, or any of the cyclododecenes; any of the monounsaturated structures derivable from myrcene containing a trisubstituted C=C, such as —CH$_2$(C—)[CH$_2$CH$_2$CH=C(CH$_3$)$_2$]CH(CH$_3$)—, —CH$_2$(C—)[CH$_2$CH$_2$CH=C(CH$_3$)2]CH$_2$CH$_2$—, —CH$_2$CH[CH$_2$CH$_2$CH=C(CH$_3$)$_2$](CH—)CH$_2$—, and —C(CH$_3$)[CH$_2$CH$_2$CH=C(CH$_3$)$_2$](CH—)CH$_2$—; any of the unsaturated structures derivable from myrcene, such as —CH$_2$(C—)(CH=CH$_2$)CH$_2$CH$_2$(CH—)C(CH$_3$)$_2$—, —CH$_2$C(=CHCH$_2$—)CH$_2$CH$_2$(CH—)C(CH$_3$)$_2$—, —CH$_2$(CH—)C(=CH$_2$)CH$_2$CH$_2$(CH—)C(CH$_3$)$_2$—, and —CH$_2$(C—)[CH$_2$CH$_2$CH=C(CH$_3$)$_2$](CH—)CH$_2$—; any of the saturated structures derivable from myrcene, such as —CH$_2$CH(—CHCH$_3$)CH$_2$CH$_2$(CH—)C(CH$_3$)$_2$—, —CH$_2$CH(CH$_2$CH$_2$—)CH$_2$CH$_2$(CH—)C(CH$_3$)$_2$—, —C(CH$_3$)(—CHCH$_3$)CH$_2$CH$_2$(CH—)C(CH$_3$)$_2$—,—C(CH$_3$)(CH$_2$CH$_2$—)CH$_2$CH$_2$(CH—)C(CH$_3$)$_2$—, —CH$_2$(C—)(—CHCH$_3$)CH$_2$CH$_2$(CH—)CH(CH$_3$)$_2$, —CH$_2$(C—)(—CHCH$_3$)CH$_2$CH$_2$CH$_2$C(CH$_3$)$_2$—, —CH$_2$(C—)(CH$_2$CH$_2$—)CH$_2$CH$_2$(CH—)CH(CH$_3$)$_2$, —CH$_2$(C—)(CH$_2$CH$_2$—)CH$_2$CH$_2$CH$_2$C(CH$_3$)$_2$—, —CH$_2$CH(—CHCH$_2$—)CH$_2$CH$_2$(CH—)CH(CH$_3$)$_2$, —CH$_2$CH(—CHCH$_2$—)CH$_2$CH$_2$CH$_2$C(CH$_3$)$_2$—, CH$_3$(C—)(—CHCH$_2$—)CH$_2$CH$_2$(CH—)CH(CH$_3$)$_2$, and CH$_3$(C—)(—CHCH$_2$—)CH$_2$CH$_2$CH$_2$C(CH$_3$)$_2$—; and pentaerythrityl, whose structure is C(CH$_2$—)$_4$. The preferred structures of tetradentate G include pentaerythrityl and any of the structures derivable from vinylnorbornene, such as —CH$_2$(CH—)-norbornyl(-)$_2$. Pentaerythrityl is most preferred.

Representative examples of polydentate G include any of the structures derivable from trivinylcyclohexane, such as —CH$_2$CH$_2$C$_6$H$_9$[(CH—)CH$_2$—]$_2$, —CH(CH$_3$)C$_6$H$_9$[(CH—)CH$_2$—]$_2$, and C$_6$H$_9$[(CH—)CH$_2$—]$_3$, where the notation C$_6$H$_9$ denotes any isomer of the trisubstituted cyclohexane ring; any structure derivable by pentasubstitution or hexasubstitution of cyclododecane; any of the structures derivable from myrcene, such as —C(CH$_3$)(—CHCH$_2$—)CH$_2$CH$_2$(CH—)C(CH$_3$)$_2$—, —CH$_2$CH(—

CHCH$_2$—)CH$_2$CH$_2$(CH—)C(CH$_3$)$_2$—, —CH$_2$(C—)(CH$_2$CH$_2$—)CH$_2$CH$_2$(CH—)C(CH$_3$)$_2$—, —CH$_2$(C—)(CHCH$_3$)CH$_2$CH$_2$(CH—)C(CH$_3$)$_2$—, —CH$_2$(C—)(CHCH$_2$—)CH$_2$CH$_2$(CH—)CH(CH$_3$)$_2$, —CH$_2$(C—)(CHCH$_2$—)CH$_2$CH$_2$CH$_2$C(CH$_3$)$_2$—, and —CH$_2$(C—)(CHCH$_2$—)CH$_2$CH$_2$(CH—)C(CH$_3$)$_2$—; and any of the groups derivable by halogenation and/or hydrohalogenation of squalene.

Representative examples of the hydrocarbon core polysulfide silanes of the present invention may be classified according to how many silyl groups branch out from their hydrocarbon cores. Thus, three silyl groups from a tridentate core, four silyl groups from a tetradentate core, and so forth. Representative examples of hydrocarbon-core polysulfide silanes of the present invention, with a tridentate core, include any of the isomers of tris-1,2,3-(2-triethoxysilyl-1-ethylnorbornyltetrathio)propane, tris-1,1,1-(2-triethoxysilyl-1-ethylnorbornyltetrathiomethyl)propane, tris-1,1,1-(2-triethoxysilyl-1-ethylnorbornyltetrathiomethyl)ethane, tris-1,2,3-(triethoxysilylnorbornyltetrathio)propane, tris-1,1,1-(triethoxysilylnorbornyltetrathiomethyl)propane, tris-1,1,1-(triethoxysilylnorbornyltetrathiomethyl)ethane, tris-1,2,3-(3-triethoxysilyl-1-propyltetrathio)propane, tris-1,1,1-(3-triethoxysilyl-1-propyltetrathiomethyl)propane, tris-1,1,1-(3-triethoxysilyl-1-propyltetrathiomethyl)ethane, tris-1,2,3-(2-triethoxysilyl-1-ethyltetrathio)propane, tris-1,1,1-(2-triethoxysilyl-1-ethyltetrathiomethyl)propane, tris-1,1,1-(2-triethoxysilyl-1-ethyltetrathiomethyl)ethane, tris-1,2,3-(triethoxysilylmethyltetrathio)propane, tris-1,1,1-(triethoxysilylmethyltetrathiomethyl)propane, tris-1,1,1-(triethoxysilylmethyltetrathiomethyl)ethane, tris-1,2,3-(2-triethoxysilyl-1-ethylnorbornyltrithio)propane, tris-1,1,1-(2-triethoxysilyl-1-ethylnorbornyltrithiomethyl)propane, tris-1,1,1-(2-triethoxysilyl-1-ethylnorbornyltrithiomethyl)ethane, tris-1,2,3-(triethoxysilylnorbornyltrithio)propane, tris-1,1,1-(triethoxysilylnorbornyltrithiomethyl)propane, tris-1,1,1-(triethoxysilylnorbornyltrithiomethyl)ethane, tris-1,2,3-(3-triethoxysilyl-1-propyltrithio)propane, tris-1,1,1-(3-triethoxysilyl-1-propyltrithiomethyl)propane, tris-1,1,1-(3-triethoxysilyl-1-propyltrithiomethyl)ethane, tris-1,2,3-(2-triethoxysilyl-1-ethyltrithio)propane, tris-1,1,1-(2-triethoxysilyl-1-ethyltrithiomethyl)propane, tris-1,1,1-(2-triethoxysilyl-1-ethyltrithiomethyl)ethane, tris-1,2,3-(triethoxysilylmethyltithio)propane, tris-1,1,1-(triethoxysilylmethyltetrathiomethyl)propane, tris-1,1,1-(triethoxysilylmethyltrithiomethyl)ethane, tris-1,2,3-(2-triethoxysilyl-1-ethylnorbornyldithio)propane, tris-1,1,1-(2-triethoxysilyl-1-ethylnorbornyldithiomethyl)propane, tris-1,1,1-(2-triethoxysilyl-1-ethylnorbornyldithiomethyl)ethane, tris-1,2,3-(triethoxysilylnorbornyldithio)propane, tris-1,1,1-(triethoxysilylnorbornyldithiomethyl)propane, tris-1,1,1-(triethoxysilylnorbornyldithiomethyl)ethane, tris-1,2,3-(3-triethoxysilyl-1-propyldithio)propane, tris-1,1,1-(3-triethoxysilyl-1-propyldithiomethyl)propane, tris-1,1,1-(3-triethoxysilyl-1-propyldithiomethyl)ethane, tris-1,2,3-(2-triethoxysilyl-1-ethyldithio)propane, tris-1,1,1-(2-triethoxysilyl-1-ethyldithiomethyl)propane, tris-1,1,1-(2-triethoxysilyl-1-ethyldithiomethyl)ethane, tris-1,2,3-(triethoxysilylmethyldithio)propane, tris-1,1,1-(triethoxysilylnethyldithiomethyl)propane, tris-1,1,1-(triethoxysilylmethyldithiomethyl)ethane, 2-[bis(2-triethoxysilyl-1-ethylnorbornyltetrathio)norbornylethyltetrathio]-1-ethylnorbornyltriethoxysilane, 2-[bis(2-triethoxysilyl-1-ethylnorbornyltetrathio)cyclohexylethyltetrathio]-1-ethylnorbornyltriethoxysilane, 2-[bis(2-triethoxysilyl-1-ethylnorbornyltetrathio)(methylcyclohexyl)isopropyltetrathio]-1-ethylnorbornyltriethoxysilane, bis(triethoxysilylnorbornyltetrathio)norbornylethyltetrathionorbornyltriethoxysilane, bis(triethoxysilylnorbornyltetrathio)cyclohexylethyltetrathionorbornyltriethoxysilane, bis(triethoxysilylnorbornyltetrathio)(methylcyclohexyl)isopropyltetrathionorbornyltriethoxysilane, 3-[bis(3-triethoxysilyl-1-propyltetrathio)norbornylethyltetrathio]-1-propyltriethoxysilane, 3-[bis(3-triethoxysilyl-1-propyltetrathio)cyclohexylethyltetrathio]-1-propyltriethoxysilane, 3-[bis(3-triethoxysilyl-1-propyltetrathio)(methylcyclohexyl)isopropyltetrathio]-1-propyltriethoxysilane, 2-[bis(2-triethoxysilyl-1-pethyltetrathio)norbornylethyltetrathio]-1-ethyltriethoxysilane, 2-[bis(2-triethoxysilyl-1-ethyltetrathio)cyclohexylethyltetrathio]-1-ethyltriethoxysilane, 2-[bis(2-triethoxysilyl-1-ethyltetrathio)(methylcyclohexyl)isopropyltetrathio]-1-ethyltriethoxysilane, bis(triethoxysilylmethyltetrathio)norbornylethyltetrathiomethyltriethoxysilane, bis(triethoxysilylmethyltetrathiocyclo)hexylethyltetrathiomethyltriethoxysilane, bis(triethoxysilyhnethyltetrathio)(methylcyclohexyl)isopropyltetrathiomethyltriethoxysilane, 3-[bis(2-triethoxysilyl-1-ethyltetrathio)norbornylethyltetrathio]-1-propyltriethoxysilane, 3-[bis(2-triethoxysilyl-1-ethyltetrathio)cyclohexylethyltetrathio)-1-propyltriethoxysilane, 3-[bis(2-triethoxysilyl-1-ethyltetrathio)(methylcyclohexyl)isopropyltetrathio]-1-propyltriethoxysilane, 3-[bis(triethoxysilylmethyltetrathio)norbornylethyltetrathio]-1-propyltriethoxysilane, 3-[bis(triethoxysilylmethyltetrathio)cyclohexylethyltetrathio]-1 -propyltriethoxysilane, 3-[bis(triethoxysilyhnethyltetrathio)(methylcyclohexyl)isopropyltetrathio]-1-propyltriethoxysilane, 2-[bis(triethoxysilylmethyltetrathio)norbornylethyltetrathio]-1-ethyltriethoxysilane, 2-[bis(triethoxysilylmethyltetrathio)cyclohexylethyltetrathio]-1-ethyltriethoxysilane, 2-[bis(triethoxysilylmethyltetrathio)(methylcyclohexyl)isopropyltetrathio]-1-ethyltriethoxysilane, [bis(2-triethoxysilyl-1-ethylnorbornyltetrathio)ethyl](2-triethoxysilyl-1-ethylnorbornyltetrathioethyl)benzene, tris(2-triethoxysilyl-1-ethylnorbornyltetrathio)cyclopentane, hydrodicyclopentadiene tris(2-tetrathionorbornyl-1-ethyltriethoxysilane), [bis(triethoxysilylnorbornyltetrathio)ethyl](triethoxysilylnorbornyltetrathioethyl)benzene, tris(triethoxysilylnorbornyltetrathio)cyclopentane, hydrodicyclopentadiene tris(tetrathionorbornyltriethoxysilane), [bis(3-triethoxysilyl-1-propyltetrathio)ethyl](3-triethoxysilyl-1-propyltetrathioethyl)benzene, tris(3-triethoxysilyl-1-propyltetrathio)cyclopentane, hydrodicyclopentadiene tris(3-tetrathio-1-propyltriethoxysilane), [bis(2-triethoxysilyl-1-ethyltetrathio)ethyl](2-triethoxysilyl-1-ethyltetrathioethyl)benzene, tris(2-triethoxysilyl-1-ethyltetrathio)cyclopentane, hydrodicyclopentadiene tris(2-tetrathio-1-ethyltriethoxysilane), [bis(triethoxysilylmethyltetrathio)ethyl](triethoxysilylmethyltetrathioethyl)benzene, tris(triethoxysilylmethyltetrathio)cyclopentane, hydrodicyclopentadiene tris(tetrathiomethyltriethoxysilane), tris(2-triethoxysilyl-1-ethylnorbornyltetrathioethyl)cyclohexane, tris(2-triethoxysilyl-1-ethylnorbornyltetrathio)cyclododecane, 2,6-dimethyltris(2-triethoxysilyl-1-ethylnorbornyltetrathio)octane, 2-ethyl-6-methyltris(2-triethoxysilyl-1-ethylnorbornyl tetrathio)heptane, tris (triethoxysilylnorbornyltetrathioethyl)cyclohexane, tris(triethoxysilylnorbornyltetrathio)cyclododecane, 2,6-dimethyltris(triethoxysilylnorbornyltetrathio)octane, 2-ethyl-6-methyltris(triethoxysilylnorbornyltetrathio)heptane, tris(3-triethoxysilyl-1-propyltetrathioethyl)cyclohexane, tris(3-triethoxysilyl-1-propyltetrathio)cyclododecane, 2,6-dimethyltris(3-triethoxysilyl-1-propyltetrathio)octane, 2-ethyl-6-methyltris(3-riethoxysilyl-1-propyltetrathio)heptane, tris(2-riethoxysilyl-1-ethyltetrathioethyl)cyclohexane, tris(2-triethoxysilyl-1-ethyltetrathio)cyclododecane, 2,6-dimethyltris(2-triethoxysilyl-1-ethyltetrathio)octane, 2-ethyl-6-methyltris(2-triethoxysilyl-1-ethyltetrathio)heptane, tris(triethoxysilylmethyltetrathioethyl)cyclohexane, tris(triethoxysilylmethyltetrathio)cyclododecane, 2,6-dimnethyltris(triethoxysilylmethyltetrathio)octane, 2-ethyl-6-methyltris(triethoxysilylmethyltetrathio)heptane, 2,6,10,15,19,23-hexamethyltris(2-triethoxysilyl-1-ethylnorbornyltetrathio)tetracosatriene, 2,6,10,15,19,23-hexamethyltris(triethoxysilylnorbornyltetrathio)tetracosatriene, 2,6,10,15,19,23-hexamethyltris(3-triethoxysilyl-1-propyltetrathio)tetracosatriene, 2,6,10,15,19,23-hexamethyltris(3-triethoxysilyl-1-propyltetrathio)tetracosatriene, 2,6,10,15,19,23-hexamethyltris(2-triethoxysilyl-1-ethyltetrathio)tetracosatriene, and 2,6,10,15,19,23-hexamethyltris(triethoxysilylmethyltetrathio)tetracosatriene.

Representative examples of hydrocarbon-core polysulfide silanes of the present invention, with a tetradentate core, include any of the isomers of tetrakis-1,3,4,5-(2-triethoxysilyl-1-ethylnorbornyltetrathio)neopentane, tetrakis-1,3,4,5-(triethoxysilylnorbornyltetrathio)neopentane, tetrakis-1,3,4,5-(3-triethoxysilyl-1-propyltetrathio)neopentane, tetrakis-1,3,4,5-(2-triethoxysilyl-1-ethyltetrathio)neopentane, tetrakis-1,3,4,5-triethoxysilylmethyltetrathioneopentane, tetrakis-1,3,4,5-(2-triethoxysilyl-1-ethylnorbornyltrithio)neopentane, tetrakis-1,3,4,5-(triethoxysilylnorbornyltrithio)neopentane, tetrakis-1,3,4,5-(3-triethoxysilyl-1-propyltrithio)neopentane, tetrakis-1,3,4,5-(2-triethoxysilyl-1-ethyltrithio)neopentane, tetrakis-1,3,4,5-triethoxysilyhnethyltrithioneopentane, tetrakis-1,3,4,5-(2-triethoxysilyl-1-ethylnorbornyltetrathio)neopentane, tetrakis-1,3,4,5-(triethoxysilylnorbornyldithio)neopentane, tetrakis-1,3,4,5-(3-triethoxysilyl-1-propyldithio)neopentane, tetrakis-1,3,4,5-(2-triethoxysilyl-1-ethyldithio)neopentane, tetrakis-1,3,4,5-triethoxysilylmethyldithioneopentane, tetrakis-1,3,4,5-(2-methyldimethoxysilyl-1-ethylnorbornyltetrathio)neopentane, tetrakis-1,3,4,5-(methyldimethoxysilylnorbornyltetrathio)neopentane, tetrakis-1,3,4,5-(3-methyldimethoxysilyl-1-propyltetrathio)neopentane, tetrakis-,3,4,5-(2-methyldimethoxysilyl-1-ethyltetrathio)neopentane, tetrakis-1,3,4,5-methyldimethoxysilylmethyltetrathioneopentane, tetrakis-1,3,4,5-(2-methyldimethoxysilyl-1-ethylnorbornyltrithio)neopentane, tetrakis-1,3,4,5-(methyldimethoxysilylnorbornyltrithio)neopentane, tetrakis-1,3,4,5-(3-methyldimethoxysilyl-1-propyltrithio)neopentane, tetrakis-1,3,4,5-(2-methyldimethoxysilyl-1-ethyltrithio)neopentane, tetrakis-1,3,4,5-methyldimethoxysilylmethyltrithioneopentane, tetrakis-1,3,4,5-(2-methyldimethoxysilyl-1-ethylnorbornyltetrathio)neopentane, tetrakis-1,3,4,5-(methyldimethoxysilylnorbornyldithio)neopentane, tetrakis-1,3,4,5-(3-methyldimethoxysilyl-1-propyldithio)neopentane, tetrakis-1,3,4,5-(2-methyldimethoxysilyl-1-ethyldithio)neopentane, tetrakis-1,3,4,5-methyldimethoxysilylmethyldithioneopentane, bis-1,2-(2-triethoxysilyl-1-ethylnorbornyltetratbio)ethyl-bis(2-triethoxysilyl-1-ethylnorbornyltetrathio)norbornane, bis-1,2-(2-triethoxysilyl-1-ethylnorbornyltetrathio)ethyl-bis(2-triethoxysilyl-1-ethylnorbornyltetrathio)cyclohexane, methylbis-1,2-(2-trietlioxysilyl-1-ethylnorbornyltetrathio)isopropyl-bis(2-triethoxysilyl-1-ethylnorbornyltetrathio)cyclohexane, bis-1,2-(triethoxysilylnorbornyltetrathio)ethylbis(triethoxysilylnorbornyltetrathio)norbomane, bis-1,2-(triethoxysilylnorbornyltetrathio)ethylbis(triethoxysilylnorbornyltetrathio)cyclohexane, methylbis-1,2-(triethoxysilylnorbornyltetrathio)isopropyl-bis(triethoxysilylnorbornyltetrathio)cyclohexane, bis-1,2-(3-triethoxysilyl-1-propyltetrathio)ethyl-bis(3-triethoxysilyl-1-propyltetrathio)norbornane, bis-1,2-(3-triethoxysilyl-1-propyltetrathio)ethyl-bis(3-triethoxysilyl-1-propyltetrathio)cyclohexane, methylbis-1,2-(3-triethoxysilyl-1-propyltetrathio)isopropyl-bis(2-triethoxysilyl-1-ethylnorbornyltetrathio)cyclohexane, bis-1,2-(2-triethoxysilyl-1-ethyltetrathio)ethyl-bis(2-triethoxysilyl-1-ethyltetrathio)norbornane, bis-1,2-(2-triethoxysilyl-1-ethyltetrathio)ethyl-bis(2-triethoxysilyl-1-ethyltetrathio)cyclohexane, methylbis-1,2-(2-triethoxysilyl-1-ethyltetrathio)isopropyl-bis(2-triethoxysilyl-1-ethyltetrathio)cyclohexane, bis-1,2-(triethoxysilylmethyltetrathio)ethyl-bis(triethoxysilylmethyltetrathio)norbornane, bis-1,2-(triethoxysilylmnethyltetrathio)ethyl-bis(triethoxysilylmethyltetrathio)cyclohexane, methylbis-1,2-(triethoxysiiylmethyltetrathio)isopropyl-bis(triethoxysilylmethyltetrathio)cyclohexane, bis[bis-1,2-(2-triethoxysilyl-1-ethylnorbornyltetrathio)ethyl]benzene, tetrakis(2-triethoxysilyl-1-ethylnorbornyltetrathio)cyclopentane, dicyclopentadiene tetrakis(2-tetrathionorbornyl-1-ethyltriethoxysilane), bis[bis-(1,2-triethoxysilylnorbornyltetrathio)ethyl]benzene, tetrakis(triethoxysilylnorbornyltetrathio)cyclopentane, dicyclopentadiene tetrakis(tetrathionorbornyltriethoxysilane), bis[bis-1,2-(3-triethoxysilyl-1-propyltetrathio)ethyl]benzene, tetrakis(3-triethoxysilyl-1-propyltetrathio)cyclopentane, dicyclopentadiene tetrakis(3-tetrathio-1-propyltriethoxysilane), bis[bis-1,2-(2-triethoxysilyl-1-ethyltetrathio)ethyl]benzene, tetrakis(2-triethoxysilyl-1-ethyltetrathio)cyclopentane, dicyclopentadiene tetrakis(2-tetrathio-1-ethyltriethoxysilane), bis[bis-1,2-(triethoxysilylnethyltetrathio)ethyl]benzene, tetrakis(triethoxysilylmethyltetrathio)cyclopentane, dicyclopentadiene tetrakis(tetrathiomethyltriethoxysilane), tetrakis(2-triethoxysilyl-1-ethylnorbornyltetrathio)cyclododecene, tetrakis(2-triethoxysilyl-1-ethylnorbornyltetrathio)cyclododecane, 2,6-dimethyltetrakis(2-triethoxysilyl-1-ethylnorbornyltetrathio)octane, 2-ethyl-6-methyltetrakis(2-triethoxysilyl-1-ethylnorbornyltetrathio)hept-1-ene, tetrakis(triethoxysilylnorbornyltetrathio)cyclododecene, tetrakis(triethoxysilylnorbornyltetrathio)cyclododecane, 2,6-dimethyltetrakis(triethoxysilylnorbornyltetrathio)octane, 2-ethyl-6-methyltetrakis(triethoxysilylnorbornyltetrathio)hept-1-ene, tetrakis(3-triethoxysilyl-1-propyltetrathio)cyclododecene, tetrakis(3-triethoxysilyl-1-propyltetrathio)cyclododecane, 2,6-dimethyltetrakis(3-triethoxysilyl-1-propyltetrathio)octane, 2-ethyl-6-methyltetrakis(3-triethoxysilyl-1-propyltetrathio)hept-1-ene, tetrakis(2-triethoxysilyl-1-ethyltetrathio)cyclododecene, tetrakis(2-triethoxysilyl-1-ethyltetrathio)cyclododecane, 2,6-dimethyltetrakis(2-triethoxysilyl-1-ethyltetrathio)octane, 2-ethyl-6-methyltetrakis(2-triethoxysilyl-1-methyltetrathio) hept-1-ene, tetrakis(triethoxysilylmethyltetrathio) cyclododecene, tetrakis(triethoxysilylmethyltetrathio) cyclododecane, 2,6-dimethyltetrakis (triethoxysilylmethyltetrathio)octane, 2-ethyl-6-methyltetrakis(triethoxysilylmethyltetrathio)hept-1-ene, 2,6,10,15,19,23-hexamethyltetrakis(2-triethoxysilyl-1-ethylnorbornyltetrathio)tetracosadiene, 2,6,10,15,19,23-hexamethyltetrakis(triethoxysilylnorbornyltetrathio) tetracosadiene, 2,6,10,15,19,23-hexamethyltetrakis(3-triethoxysilyl-1-propyltetrathio)tetracosadiene, 2,6,10,15, 19,23-hexamethyltetrakis(3-triethoxyslyl-1-propyltetrathio) tetracosatriene, 2,6,10,15,19,23-hexamethyltetrakis(3-triethoxysilyl-1-propyltetrathio)tetracosatriene, 2,6,10,15, 19,23-hexamethyltetrakis(2-triethoxysilyl-1-ethyltetrathio) tetracosadiene, and 2,6,10,15,19,23-hexamethyltetrakis (triethoxysilylmethyltetrathio)tetracosadiene.

Representative examples of hydrocarbon-core polysulfide silanes of the present invention, with a polydentate core, include any of the isomers of pentakis(2-triethoxysilyl-1-ethylnorbornyltetrathioethyl)cyclohexane, pentakis(2-triethoxysilyl-1-ethylnorbornyltetrathio)cyclododecane, 2,6-dimethylpentakis(2-triethoxysilyl-1-ethylnorbornyltetrathio)octane, pentakis (triethoxysilylnorbornyltetrathioethyl)cyclohexane, pentakis(triethoxysilylnorbornyltetrathio)cyclododecane, 2,6-dimethylpentakis(triethoxysilylnorbornyltetrathio) octane, pentakis(3-triethoxysilyl-1-propyltetrathioethyl) cyclohexane, pentakis(3-triethoxysilyl-1-propyltetrathio) cyclododecane, 2,6-dimethylpentakis(3-triethoxysilyl-1-propyltetrathio)octane, pentakis(2-triethoxysilyl-1-ethyltetrathioethyl)cyclohexane, pentakis(2-triethoxysilyl-1-ethyltetrathio)cyclododecane, 2,6-dimethylpentakis(2-triethoxysilyl-1-ethyltetrathio)octane, pentakis (triethoxysilylmethyltetrathioethyl)cyclohexane, pentakis (triethoxysilylmethyltetrathio)cyclododecane, 2,6-dimethylpentakis(triethoxysilylmethyltetrathio)octane, 2,6, 10,15,19,23-hexamethylpentakis(2-triethoxysilyl-1-ethylnorbornyltetrathio)tetracosene, 2,6,10,15,19,23-hexamethylpentakis(triethoxysilylnorbornyltetrathio) tetracosene, 2,6,10,15,19,23-hexamethylpentakis(3-triethoxysilyl-1-propyltetrathio)tetracosene, 2,6,10,15,19, 23-hexamethylpentakis(3-triethoxysilyl-1-propyltetrathio) tetracosadiene, 2,6,10,15,19,23-hexamethylpentakis(3-triethoxysilyl-1-propyltetrathio)tetracosatriene, 2,6,10,15, 19,23-hexamethylpentakis(2-triethoxysilyl-1-ethyltetrathio) tetracosene, and 2,6,10,15,19,23-hexamethylpentakis (triethoxysilylmethyltetrathio)tetracosene; as well as hexakis(2-triethoxysilyl-1-ethylnorbornyltetrathioethyl) cyclohexane, hexakis(2-trietloxysilyl-1-ethylnorbornyltetrathio)cyclododecane, 2,6-ditnethylhexakis(2-triethoxysilyl-1-ethylnorbornyltetrathio) octane, hexakis(triethoxysilylnorbornyltetrathioethyl) cyclohexane, hexakis(triethoxysilylnorbornyltetrathio) cyclododecane, 2,6-dimethylhexakis (triethoxysilylnorbornyltetrathio)octane, hexakis(3-triethoxysilyl-1-propyltetrathioethyl)cyclohexane, hexakis (3-triethoxysilyl-1-propyltetrathio)cyclododecane, 2,6-dimethylhexakis(3-triethoxysilyl-1-propyltetrathio)octane, hexakis(2-triethoxysilyl-1-ethyltetrathioethyl)cyclohexane, hexakis(2-triethoxysilyl-1-ethyltetrathio)cyclododecane, 2,6-dimethylhexakis(2-triethoxysilyl-1-ethyltetrathio) octane, hexakis(triethoxysilylmethyltetrathioethyl) cyclohexane, hexakis(triethoxysilylnethyltetrathio) cyclododecane, 2,6-dimethylhexakis (triethoxysilylmethyltetrathio)octane, 2,6,10,15,19,23-hexamethylhexakis(2-triethoxysilyl-1-ethylnorbornyltetrathio)tetracosane, 2,6,10,15,19,23-hexamethylhexakis(triethoxysilylnorbornyltetrathio) tetracosane, 2,6,10,15,19,23-hexamethylhexakis(3-triethoxysilyl-1-propyltetrathio)tetracosane, 2,6,10,15,19, 23-hexamethylhexakis( 3-triethoxysilyl-1-propyltetrathio) tetracosene, 2,6,10,15,19,23-hexamethiylhexakis(3-triethoxysilyl-1-propyltetrathio)tetracosadiene, 2,6,10,15, 19,23-hexamethylhexakis(3-triethoxysilyl-1-propyltetrathio)tetracosatriene, 2,6,10,15,19,23-hexamethylhiexakis(2-triethoxysilyl-1-ethyltetrathio) tetracosane, and 2,6,10,15,19,23-hexamethylhexakis (triethoxysilylmethyltetrathio)tetracosane.

The preferred embodiments of thle present invention include compositions comprising at least one of any of the isomers of tris-1,2,3-(2-triethoxysilyl-1-ethylnorbornyltetrathio)propane, tris-1,1,1-(2-triethoxysilyl-1-ethylnorbornyltetrathiomethyl)propane, tris-1,1,1-(2-triethloxysilyl-1-ethylnorbornyltetrathiomethyl)ethane, tris-1,2,3-(triethloxysilylnorbornyltetrathio)propane, tris-1,1,1-(triethoxysilylnorbornyltetrathiomethyl)propane, tris-1,1,1-(triethoxysilylnorbornyltetrathiomethyl)ethane, tris-1,2,3-(3-trietiloxysilyl-1-propyltetrathio)propane, tris-1,1,1-(3-triethoxysilyl-1-propyltetrathiomethyl)propane, tris-1,1,1-(3-trietlioxysilyl-1-propyltetrathiomethyl)ethane, tris-1,2,3-(2-triethloxysilyl-1-ethyltetrathio)propane, tris-1,1,1-(2-triethoxysilyl-1-ethyltetrathiomethyl)propane, tris-1,1,1-(2-triethoxysilyl-1-ethyltetrathiomethyl)ethane, tris-1,2,3-(triethloxysilylmethyltetrathio)propane, tris-1,1,1-(triethoxysilylmethyltetrathiomethyl)propane, tris-1,1,1-(triethoxysilylmnethyltetrathiomethyl)ethane, tris(2-triethoxysilyl-1-ethylnorbornyltetrathio)cyclododecane, 2,6-dimethlyltris(2-trietiloxysilyl-1-ethylnorbornyltetrathio)octane, 2-ethyl-6-methyltris(2-triethloxysilyl-1-ethylnorbornyltetrathio)heptane, 2,6-dimethyltris(triethloxysilylnorbornyltetrathio)octane, 2-ethyl-6-methlyltris(triethoxysilylnorbornyltetrathio) heptane, tris(3-triethoxysilyl-1-propyltetrathiio) cyclododecane, 2,6-dimethyltris(3-triethoxysilyl-1-propyltetrathio)octane, 2-ethyl-6-methyltris(3-triethoxysilyl-1-propyltetrathio)heptane, tris(2-triethoxysilyl-1-ethyltetrathio)cyclododecane, 2,6-dimethyltris(2-triethoxysilyl-1-ethyltetrathio)octane, 2-ethyl-6-methyltris(2-triethoxysilyl-1-ethyltetrathio) heptane, tris(triethoxysilylmethyltetrathio)cyclododecane, 2,6-dimethyltris(triethoxysilylmethyltetrathio)octane, 2-ethyl-6-methyltris(triethoxysilylmethyltetrathio)heptane; any of the isomers of tetrakis-1,3,4,5-(2-triethoxysilyl-1-ethylnorbornyltetrathio)neopentane, tetrakis-1,3,4,5-(triethoxysilylnorbornyltetrathio)neopentane, tetrakis-1,3,4, 5-(3-triethoxysilyl-1-propyltetrathio)neopentane, tetrakis-1, 3,4,5-(2-triethoxysilyl-1-ethyltetrathio)neopentane, tetrakis-1,3,4,5-triethoxysilylmethyltetrathioneopentane, tetrakis-1, 3,4,5-(3-triethoxysilyl-1-propyltrithio)neopentane, tetrakis-1,3,4,5-(3-triethoxysilyl-1-propyldithio)neopentane, tetrakis (2-triethoxysilyl-1-ethylnorbornyltetrathio)cyclododecane, 2,6-dimethyltetrakis(2-triethoxysilyl-1-ethylnorbornyltetrathio)octane, tetrakis (triethoxysilylnorbornyltetrathio)cyclododecane, 2,6-dimethyltetrakis(triethoxysilylnorbornyltetrathio)octane, tetrakis(3-triethoxysilyl-1-propyltetrathio)cyclododecane, 2,6-dimethyltetrakis(3-triethoxysilyl-1-propyltetrathio) octane, tetrakis(2-triethoxysilyl-1-ethyltetrathio) cyclododecane, 2,6-dimethyltetrakis(2-triethoxysilyl-1-ethyltetrathio)octane, tetrakis(triethoxysilylmethyltetrathio) cyclododecane, 2,6-dimethyltetrakis (triethoxysilylmethyltetrathio)octane; and any of the isomers of 2,6,10,15,19,23-hexamethylpentakis(3-triethoxysilyl-1-propyltetrathio)tetracosene and 2,6,10,15,19,23-hexamethylhexakis(3-triethoxysilyl-1-propyltetrathio)tetracosane.

Especially preferred embodiments of the present invention include compositions comprising at least one of the isomers of tris-1,2,3-(3-triethoxysilyl-1-propyltetrathio)propane, tris-1,1,1-(3-triethoxysilyl-1-propyltetrathiomethyl)propane, tris-1,1,1-(3-triethoxysilyl-1-propyltetrathiomethyl)ethane, tetrakis-1,3,4,5-(3-triethoxysilyl-1-propyltetrathio)neopentane, and tetrakis-1,3,4,5-(2-triethoxysilyl-1-ethyltritiio)neopentane. Tetrakis-1,3,4,5-(3-triethoxysilyl-1-propyltetrathio)neopentane being most preferred.

Included within the scope of the invention are the partial hydrolyzates and condensates of the above referenced hydrocarbon core polysulfide silanes. The partial hydrolyzates and condensates may be present in an amount of up to about 10 wt. % of the polysulfide silanes. Higher amounts of hydrolyzates or condensates will work but usually with reduced efficacy in comparison to the monomers.

A general method of preparing the hydrocarbon core polysulfide silanes of the present invention may be categorized by the type of base used to deprotonate a mercaptan starting material and how the silicon functionality is introduced into the final composition. Equation sequence 1 illustrates the reactions to form the hydrocarbon core polysulfide silanes of the present invention wherein the silyl group is introduced via the mercaptan.

Equation Sequence 1

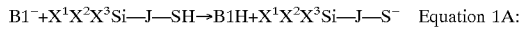  Equation 1A:

or

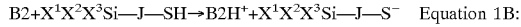  Equation 1B:

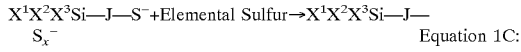  Equation 1C:

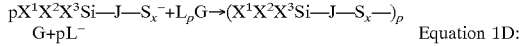  Equation 1D:

Category I reactions involve an anionic base, B1$^-$, which functions as a Brönsted base and includes alkoxides. Brönsted bases are those bases which accept one or more protons. Alternatively, Category II reactions involve neutral Brönsted bases or non-ionic Brönsted bases such as amines. In both Category I and II reactions, the silyl group is introduced via the mercaptan while the hydrocarbon core is introduced via the substrate L$_p$G or X$^1$X$^2$X$^3$Si—J—L, the substrate containing carbon and the leaving group L which is reactive with sulfur anions.

Equation sequence 2 illustrates how the hydrocarbon core polysulfide silanes of the present invention are formed when the silicon functionality is introduced via so the substrate.

Equation Sequence 2

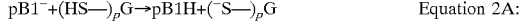  Equation 2A:

or

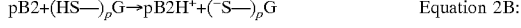  Equation 2B:

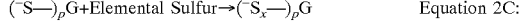  Equation 2C:

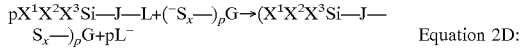  Equation 2D:

Category III reactions utilize an anionic Brönsted base while Category IV reactions involve non-ionic Brönsted bases such as amines.

Equation sequences 1 and 2 start with a desired mercaptan such as X$^1$X$^2$X$^3$Si—J—SH or (HS—)$_p$G; a base capable of deprotonating the mercaptan; elemental sulfur to react with the deprotonated mercaptan X$^1$X$^2$X$^3$Si—J—S$^-$ or ($^-$S—)$_p$G to form the reactive sulfur anion X$^1$X$^2$X$^3$Si—J—S$_x^-$ or ($^-$S$_x$—)$_p$G, (the sulfur nucleophile); and a substrate to couple with the sulfur nucleophile. As shown, the base extracts a single proton from the mercaptan. However, bases capable of extracting multiple protons may also be used in which case the stoichiometry is adjusted accordingly. Thus, the desired amount of base involves p equivalents of B1$^-$ or B2 for each mole of mercaptan (HS—)$_p$G used to which is added a quantity of p(x-1) atoms of sulfur as elemental sulfur and p moles of substrate X$^1$X$^2$X$^3$Si—J—L. Preferred cationic counterions for B1$^-$ are the alkali metals, with sodium usually most preferred. Potassium ion may be preferred when using very hindered alcohols and/or alkoxides are used as the base and/or solvent (e.g. tert-butoxy). In cases involving ether solvents, lithium ion may be preferred. The values of x and p, as well as the structures X$^1$, X$^2$, X$^3$, J and G are those specified in Formula I.

L may be any group whose anion, L$^-$, is a viable leaving group. Examples of L$^-$ include, but are not limited to, chloride, bromide, iodide, sulfate, trifluoroacetate, and any of the sulfonates including tosylate, benzenesulfonate, and triflate. Chloride is preferable due to its commercial availability. Bromide is preferable in cases wherein enhanced reactivity relative to the chloride is desired, such as in aromatic halogen substitutions, which require more rigorous conditions.

The preferred solvents for the preparation of the hydrocarbon core polysulfide silanes of the present invention typically are protic solvents, such as alcohols and amines because they readily dissolve and/or promote the formation of the sulfur anions, mediate the chemical reactions readily, and lead to anionic coproducts which are most easily removed from the product. Representative examples of suitable protic solvents include methanol, ethanol, n-propanol, isopropanol, n-butanol, sec-butanol, t-butanol, butylamine, ethylene diamine, diethylene triamine, and the like. Aprotic solvents, may be used as well including ethers, tetrahydrofuran, polyethers, glyme, diglyme and higher glymes, aromatic solvents such as toluene and xylene provided that the sulfur anion is sufficiently soluble, dimethylformamide, dimethylsulfoxide, N-methylpyrrolidinone, and tertiary amines such as triethylamine. N-methylpyrrolidinone is preferred for substitutions directly on aromatic rings. In some cases, solventless systems may also be used.

An advantage of alcoholic solvents is that the preparation of the hydrocarbon core polysulfide silanes of the present invention can also be coupled with a transesterification of the alkoxy group present on the starting silane by using or substituting the solvent with another alcohol at any step prior to solvent removal. The distillation of the alcohol from the mixture can be accompanied by an exchange of the alkoxy group on silicon in which it is replaced by the alkoxy group corresponding to the alcohol solvent introduced. Thus, less volatile alcohols readily displace alkoxy groups corresponding to the more volatile alcohol groups. The reverse can also be accomplished, but requires at least two coupled distillations. An example would be the use of 3-mercapto-1-propyltrimethoxysilane with methanolic sodium methoxide, sulfur, and pentaerythritol tetrachloride in ethanol, removing the solvent by fractional distillation and generating an ethoxy hydrocarbon core polysulfide silane.

Suitable conditions for preparation of the hydrocarbon core polysulfide silanes of the present invention include reaction temperatures of about 0° C. to the reflux temperature of the solvent depending upon the concentration of reagents and pressure employed. Thus, the reaction temperature may be as high as about 190° C. or even about 200° C. if, for example, solvents such as dimethylsulfoxide or N-methylpyrrolidinone are used. Reaction temperatures between 30° C. and 80° C. are more typical conditions. Ambient pressures are generally preferred.

The logistics for preparation of the hydrocarbon core polysulfide silanes of the present invention are generally aimed at completing the formation of the polysulfidic sulfur anion from the deprotonated mercaptan prior to the introduction of the substrate. In cases where strong bases, such as alkoxides, are used to deprotonate the mercaptan, it is also desirable to deprotonate the mercaptan prior to the introduction of the sulfur source so that dark colors and the impurities associated with them are minimized. Thus, a preferred order of addition of raw materials to the reactor typically begins with an initial charge of base and mercaptan, followed by introduction of the elemental sulfur. It is sometimes desirable, but not necessary, to charge the mercaptan after the base if alkoxides are used as the base. This allows for the in-situ preparation of an appropriate solution of the base, as for example, the reaction of metallic sodium with an alcohol such as ethanol. The base and mercaptan are preferably stirred to a homogeneous solution before the elemental sulfur is introduced. Since the dissolution and reaction of the elemental sulfur to form the polysulfidic sulfur anion is not instantaneous, but occurs over a period of time, it is advantageous to use a powdered form of elemental sulfur and elevate the temperature of the mixture with continuous stirring to accelerate the dissolution process. A preferable method involves stirring the base, mercaptan and elemental sulfur at temperatures of about 40° C. to about 80° C., which typically brings about complete dissolution of powdered elemental sulfur in a few hours or less. The substrate is then added to this solution, preferably with stirring and at a controlled rate, to control the resulting exothermic reaction. Precipitated co-products are then removed by such processes as centrifugation, filtration, decantation, and the like. Any solvents present may then be removed by an evaporative process, such as distillation, stripping, rotary evaporation, etc.

Individual details for reagents, reaction conditions, and logistics suitable for preparation of the hydrocarbon core polysulfide silanes of the present invention depend on which of the four preparation categories described above. Category I preparations wherein the silyl group is introduced via the mercaptan, which involve the deprotonation of a mercapto-functional silane using an anionic base, are preferably done in the alcohol corresponding to the desired silane alkoxy group in the final product. Nearly anhydrous, and preferably strictly anhydrous alcohols and conditions need to be used throughout the process. Although any base strong enough to deprotonate the mercaptan can be used, it is preferable to use an alkali metal alkoxide, more preferably sodium alkoxide, wherein the alkoxide corresponds to the silane alkoxy group of the desired final product. For example, if an ethoxy silane product is desired, one would preferably deprotonate the starting mercapto-functional silane with ethanolic sodium ethoxide. Although the alkali metal alkoxide could be added to the mercapto-functional silane, it is preferable to initially prepare an alcoholic solution of the alkali metal alkoxide, to which the mercapto-functional silane is then added. The alcoholic solution of the alkali metal alkoxide can be prepared by directly reacting a suitable sodium compound with the alcohol, for example sodium metal, sodium hydride, etc., or by dissolving the alkali metal alkoxide in the alcohol. An alternative method would involve the addition of the aforementioned sodium compound, sodium metal, or sodium alkoxide directly to an alcoholic solution of the mercapto-functional silane. In either case, the deprotonation of the mercapto-functional silane is complete upon complete mixing with the base. Elemental sulfur is now added to the deprotonated mercapto-functional silane forming the desired reactive nucleophile. After heating and stirring the mixture to accelerate the dissolution process as much as possible, the substrate is then added to this solution and the reaction worked up accordingly to remove precipitated salts and solvents.

Category II preparations wherein the silyl group is introduced via the mercaptan, involve a non-anionic base such as an amine to direct the deprotonation of a mercapto-functional silane or a deprotonation coupled with a sulfur anion displacement reaction. These preparations may be done in any of the solvents as described above. It is preferred that the preparations be done under nearly anhydrous conditions, most preferably under strictly anhydrous conditions. Neat systems, where no solvents are used or systems using an excess of the amine base as the solvent are also viable. Preferably, the solvents are chosen which minimize the solubility of the protonated amine salts co-produced in the process. Thus, ethers such as glyme and tetrahydrofuran would be preferred. Alcohols may also be used, but an additional step may be needed to precipitate residual amine salts remaining in the product by using a less polar co-solvent, such as the aforementioned ethers or perhaps toluene. It is recommended that the substrate be added only after the elemental sulfur has had a chance to substantially react with or at least reach equilibrium with a mixture of the mercapto-functional silane and the base. Thus, it is preferable for the substrate to be added last at a rate in which the resulting exothermic reaction is controlled. Again, a powdered form of the elemental sulfur is preferred with stirring at elevated temperatures of the mixture to accelerate the dissolution process as much as possible. Any resulting ionic phase is then removed by centrifugation, filtration, and/or decantation. Any remaining solvent and/or excess base is then removed by an evaporative process, such as distillation, stripping, rotary evaporation, and the like. Any amine salts which were carried in solution prior to the evaporative removal of solvent and/or excess base and which subsequently separated during the evaporative process are then removed by a second centrifugation, filtration, and/or decantation.

Category III preparations wherein the silyl group is introduced via the substrate, which involve the deprotonation of a mercaptan using an anionic base, are preferably done in an alcohol corresponding to the desired silane alkoxy group in the final product. Strictly anhydrous conditions are not necessary. Water may be present in small to modest amounts, up to about 10 wt. %, preferably no more than 5 wt. %, prior to the addition of the silicon-containing substrate. However, it is preferred that any water present be removed from the system prior to the addition of the silicon-containing substrate. Although any base strong enough to deprotonate the mercaptan may be used, an alkali metal alkoxide is preferred, more preferably the sodium alkoxide. In some cases, alkali metal hydroxides may also be used as the base. If an alkoxide is used, it should correspond to the silane alkoxy group of the desired final product. For example, if an ethoxy silane product is desired, one would preferably deprotonate the starting mercaptan with ethanolic sodium ethoxide. Although the alkali metal alkoxide or hydroxide may be added to the mercaptan, it is preferable to initially prepare an alcoholic solution thereof, to which the mercaptan is then added. The alcoholic solution of the alkali metal alkoxide may be prepared by directly reacting a suitable sodium compound with the alcohol, for example sodium metal, sodium hydride, etc., or by dissolving the alkali metal alkoxide in the alcohol. Alternatively, an alcoholic solution of the alkali metal hydroxide may be prepared by simply dissolving the hydroxide in the alcohol. Another method would involve the addition of the aforementioned sodium compound, sodium metal, sodium alkoxide, or sodium hydroxide directly to an alcoholic solution of the mercaptan. In either case, the deprotonation of the mercaptan is complete upon complete mixing with the base. Powdered elemental sulfur is now added to form the desired reactive nucleophile with heated stirring to bring about complete dissolution of powdered elemental sulfur in a few hours or less. Any water present in the system should be removed at this point according to known methods in the art. The silicon-containing substrate is then added to this solution, preferably with stirring and at a controlled rate so as to control the resulting exothermic reaction. The reaction mixture is again worked up accordingly.

Category IV preparations wherein the silyl group is introduced via the substrate, involve the direct deprotonation of a mercaptan or a deprotonation coupled with a sulfur anion displacement reaction, in either case, using a non-anionic base such as an amine. A variety of solvents may be used as described above. Strictly anhydrous conditions are not necessary. Water may be present in small to modest amounts, up to about 10 wt. %, preferably no more than 5 wt. %, prior to the addition of the silicon-containing substrate. However, any water present must be removed from the system prior to the addition of the silicon-containing substrate. Neat systems, where no solvents are used or systems using an excess of the amine base as the solvent are also viable. Preferred are solvents which minimize the solubility of the protonated amine salts co-produced in the process such as ethers, e.g., glyme, and tetrahydrofuran. Alcohols may also be used, but an additional step may be needed to precipitate residual amine salts remaining in the product by using a less polar co-solvent such as the aforementioned ethers or toluene. It is preferred that the substrate be added only after the elemental sulfur has had a chance to substantially react with or at least reach equilibrium with a mixture of the mercapto-functional silane and the base. Thus, it is preferable to add the silicon-containing substrate last. A powdered form of the elemental sulfur is preferred with continuous stirring at elevated temperatures to accelerate the dissolution process as much as possible. Any water present in the system should be removed at this point according to known methods in the art. If the amine base has a boiling point below about 100° C., the water removal process may remove the amine, thereby necessitating its replacement. The silicon-containing substrate is then added to the resulting solution, preferably with stirring and at a controlled rate so as to control the resulting exothermic reaction. The reaction is worked up as previously described.

Elastomers useful with the hydrocarbon core polysulfide silanes of the present invention include sulfur vulcanizable rubbers having conjugated diene homopolymers and copolymers, and copolymers of at least one conjugated diene and aromatic vinyl compound.

One example of a suitable polymer for use herein is solution-prepared styrene-butadiene rubber (SSBR). This solution-prepared SSBR preferably has a bound styrene content in a range of about 5 to about 50%, more preferably about 9 to 36%. Other useful polymers include styrene-butadiene rubber (SBR), natural rubber (NR), ethylene-propylene copolymers and terpolymers (EP, EPDM), acrylonitrile-butadiene rubber (NBR), polybutadiene (BR), and so forth. The rubber composition is preferably comprised of at least one diene-based elastomer, or rubber. Suitable conjugated dienes are isoprene and 1,3-butadiene and suitable vinyl aromatic compounds are styrene and alpha methyl styrene. Polybutadiene may be characterized as existing primarily, typically about 90 wt. %, in the cis-1,4-butadiene form.

Preferably, the rubber is a sulfur curable rubber. Such diene based elastomer, or rubber, may be selected, for example, from at least one of cis-1,4-polyisoprene rubber (natural and/or synthetic, preferably natural), natural rubber, emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (about 35 to about 50% vinyl), high vinyl polybutadiene rubber (about 50 to about 75% vinyl), styrene/isoprene copolymers, emulsion polymerization prepared styrene/butadiene/acrylonitrile terpolymer rubber and butadiene/acrylonitrile copolymer rubber.

For some applications, an emulsion polymerization derived styrene/butadiene (E-SBR) having a relatively conventional styrene content of about 20 to about 28% bound styrene, or an E-SBR having a medium to relatively high bound styrene content of about 30 to about 45 % may be used. Emulsion polymerization prepared styrene/butadiene/acrylonitrile terpolymer rubbers containing about 2 to about 40 wt. % bound acrylonitrile in the terpolymer are also contemplated as diene based rubbers for use in this invention.

A particulate filler may also be added to the crosslinkable elastomer compositions of the present invention including siliceous fillers, carbon black, and the like. The filler materials useful herein include, but are not limited to, carbon black, metal oxides such as silica (pyrogenic and precipitated), titanium dioxide, aluminosilicate and alumina, clays and talc, and so forth. Particulate, precipitated silica may also be used for such purpose, particularly when the silica is used in conjunction with a silane. In some cases, a combination of silica and carbon black is utilized for reinforcing fillers for various rubber products, including treads for tires. Alumina can be used either alone or in combination with silica. The term, alumina, is defined herein as aluminum oxide, or $Al_2O_3$. The alumina fillers may be hydrated or in anhydrous form.

The hydrocarbon core polysulfide silanes may be pre-mixed or pre-reacted with the filler particles, or added to the rubber mix during the rubber and filler processing, or mixing stages. If the hydrocarbon core polysulfide silanes and filler are added separately to the rubber mix during the rubber and filler mixing, or processing stage, it is considered that the hydrocarbon core polysulfide silane(s) then combine in an in-situ fashion with the filler. The polysulfide silanes of the present invention may be carried on low reactivity fillers such as carbon black.

The resultant vulcanized rubber composition having the hydrocarbon core polysulfide silanes of the present invention preferably contain a sufficient amount of filler to exhibit a reasonably high modulus and high resistance to tear. The combined weight of the filler may be as low as about 5 to about 100 parts per hundred rubber (phr), more preferably from about 25 to about 85 phr.

Preferably, at least one precipitated silica is utilized as a filler. The silica may be characterized by having a BET surface area, as measured using nitrogen gas, preferably in the range of about 40 to about 600 m$^2$/g, and more preferably in a range of about 50 to about 300 m$^2$/g. The BET method of measuring surface area is described in the *Journal of the American Chemical Society*, Volume 60, page 304 (1930). The silica typically may also be characterized by having a dibutylphthalate (DBP) absorption value in a range of about 100 to about 350, and more preferably from about 150 to about 300. Furthermore, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of 9. The method is described in ASTM D 3849.

Mercury porosity surface area is the specific surface area determined by mercury porosimetry. Using this method, mercury is penetrated into the pores of the sample after a thermal treatment to remove volatiles. Set up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39 (1959) or according to DIN 66133. For such an evaluation, a CARLO-ERBA Porosimeter 2000 might be used. The preferred average mercury porosity specific surface area for the silica is about 100 to about 300 m$^2$/g. A suitable pore size distribution for the silica, alumina and aluminosilicate according to such mercury porosity evaluation is considered herein to be such that about 5% or less of its pores have a diameter of less than about 10 nm, about 60 to 90% of its pores have a diameter of about 10 to about 100 nm, about 10 to 30% of its pores have a diameter of about 100 to about 1000 nm, and about 5 to 20% of its pores have a diameter of greater than about 1000 nm.

The silica may have an average ultimate particle size, for example, in the range of about 10 to 50 nm as determined by an electron microscope, although the silica particles may be even smaller, or possibly larger, in size. Various commercially available silicas may be considered for use in this invention, for example, HI-SIL™ 210, 243, etc. from PPG Industries of Pittsburgh, Pa.; ZEOSIL™ 1165MP from Rhodia, Inc. of Cranbury, N.J., amongst others.

In compositions for which it is desirable to utilize siliceous fillers such as silica, alumina and/or aluminosilicates in combination with carbon black reinforcing pigments, the compositions may comprise a filler mix of about 15 to about 98 wt. % siliceous filler, and about 2 to about 85 wt. % carbon black, wherein the carbon black has a CTAB value in a range of about 80 to about 150. The weight ratio may range from about 3:1 to about 30:1 for siliceous fillers to carbon black. More typically, it is desirable to use a weight ratio of siliceous fillers to carbon black of at least about 3:1, and preferably at least about 10:1. Alternatively, the filler can be comprised of about 60 to about 95 wt. % silica, alumina and/or aluminosilicate and, correspondingly, about 40 to about 5 wt. % carbon black. The siliceous filler and carbon black may be pre-blended or blended together during manufacture of the vulcanized rubber. Alternately, a portion of the carbon black may be a grade having an extremely high surface area up to about 800 m$^2$/g.

In preparing the rubber compositions of the present invention, one or more of the hydrocarbon core polysulfide silanes of the present invention are mixed with the organic polymer before, during or after the compounding of the filler into the organic polymer. It is preferable to add at least a portion of the hydrocarbon core polysulfide silanes before or during the compounding of the filler into the organic polymer, because these silanes facilitate and improve the dispersion of the filler. The total amount of hydrocarbon core polysulfide silane present in the resulting combination should be about 0.05 to about 25 phr; more preferably 1 to 10 phr. Fillers may be used in quantities ranging from about 5 to about 100 phr, more preferably from 25 to 80 phr.

A novel rubber composition utilizing the hydrocarbon core polysulfide silane of the present invention may therefore comprise about 100 parts of at least one sulfur vulcanizable rubber and copolymers of at least one conjugated diene and aromatic vinyl compound, about 5 to 100 phr, preferably about 25 to 80 phr of at least one particulate filler, up to about 5 phr of a curing agent, and about 0.05 to about 25 phr of at least one hydrocarbon core polysulfide silane.

The filler preferably comprises from about 1 to about 85 wt. % carbon black based on the total weight of the filler, and about 0.1 to about 20 wt. % of at least one hydrocarbon core polysulfide silane based on the total weight of the filler.

In another embodiment, a rubber composition of the present invention may be prepared by blending rubber, filler and hydrocarbon core polysulfide silane in a thermomechanical mixing step to a temperature of about 140° C. to about 190–200° C. for about 2 to 20 minutes, preferably about 4 to 15 minutes. Additional thermomechanical mixing steps may be performed with intermittent cooling of the rubber which may be accomplished by removing the rubber from the mixer. The filler may be pretreated with all or a portion of the hydrocarbon core polysulfide silane prior to a first thermomechanical mixing stage. Optionally, a curing agent is then added in a separate thermomechanical mixing step at a temperature of about 50° C. for about 1 to about 30 minutes. The temperature is then raised to about 130° C., up to about 200° C., and curing is accomplished in about 5 to about 60 minutes. Thus, a tire assembly with tread may be prepared accordingly and cured or vulcanized at about 130° C. to 200° C. Optional ingredients may be added to the rubber compositions of the present invention including curing agents, i.e., sulfur compounds, including activators, retarders and accelerators, processing additives such as oils, plasticizers, tackifing resins, silicas, other fillers, pigments, fatty acids, zinc oxide, waxes, antioxidants and antiozonants, peptizing agents, reinforcing materials, i.e., carbon black, and the like. Such additives are selected based upon the intended use and on the sulfur vulcanizable material selected for use, and such selection is within the knowledge of one skilled in the art, as are the required amounts of such additives.

The examples presented below demonstrate significant advantages of the silanes described herein relative to those of prior art coupling agents in silica-filled rubber.

EXAMPLE 1

Preparation of a tetrakis-1,3,4,5-(3-triethoxysilyl-1-propyltetrathio)neopentane composition (Silane 1)

An apparatus was set up which consisted of a two-neck 5-liter flask, of which one neck was fitted to a condenser and the other neck was fitted to a dropping funnel which had a vapor bypass tube for pressure equalization. The dropping funnel was capable of delivering a variable and controllable flow of liquid. The top of the condenser was fitted to a nitrogen bubbler. Heat was supplied to the flask using an electric heating mantle regulated by a variable voltage controller. The voltage controller was coupled to an electronic temperature regulator responsive to the height of mercury in a mercury thermometer. The thermometer was inserted directly into the contents of the 5-liter flask. Stirring was accomplished using a Teflon-coated stir bar. The system was maintained under an atmosphere of nitrogen using a nitrogen bubbler. Solids were removed from the reaction products, prior to the removal of solvent, by gravity filtration through a sintered glass frit in a vessel equipped to maintain its contents under inert atmosphere. Solvent was removed from the product by distillation at reduced pressure using a rotary evaporator. Smaller amounts of solids which formed during the solvent removal were removed from the product by decantation.

The entire apparatus was placed and kept under an atmosphere of dry nitrogen throughout the following procedure. Anhydrous sodium ethoxide (92.0 g, 1.35 moles) in the form of a 21 wt. % solution (438 g, 505 mL) in anhydrous ethanol was added to the flask. 3-Mercapto-1-propyltriethoxysilane (329 g, 1.38 moles) was subsequently added with stirring. Then, powdered elemental sulfur ("flowers of sulfur") was added (133 g, 4.15 moles) to the flask with continued stirring. The mixture was brought to a gentle reflux and maintained at a gentle reflux overnight to insure that the sulfur had completely dissolved, resulting in a dark red-brown solution. A solution of pentaerythritol tetrachloride (72.5 g, 0.345 moles) in an anhydrous solvent mixture of ethanol (319 g, 406 mL) and toluene (103 g, 119 mL) was then added to the dropping funnel. This solution was then added to the stirred contents of the flask. The rate of addition was adjusted so, as to maintain a vigorous, but controlled rate of reflux from the resulting exothermic reaction. The addition was complete after 25 minutes, at which time the formation of a salt precipitate was already evident. The reflux was maintained for several more hours to bring the reaction to completion or near completion, during which time the formation of more salt precipitate was evident. The reaction mixture was then cooled to ambient temperature and filtered to remove solids. The solvent was removed by rotary evaporation at an absolute pressure of less than 1 torr at 65° C., whereupon a smaller additional quantity of solid precipitate appeared, which was subsequently removed from the resulting dark red liquid by decantation.

EXAMPLE 2
Preparation of a tris-1,2,3-(3-triethoxvsilyl-1-nropyltetrathio)propane composition (Silane 2)

An apparatus similar to that of Example 1 was used. The entire apparatus was placed and kept under an atmosphere of dry nitrogen throughout the following procedure. Anhydrous sodium ethoxide (299 g, 4.39 moles) in the form of a 21 wt. % solution (1423 g, 1639 mL) in anhydrous ethanol was added to the flask. 3-Mercapto-1-propyltriethoxysilane (1071 g, 4.49 moles) was subsequently added with stirring. Then, powdered elemental sulfur ("flowers of sulfur") was added (432 g, 13.5 moles) to the flask with continued stirring. The mixture was brought to a gentle reflux and maintained at a gentle reflux for about 40 hours to insure that the sulfur had completely dissolved, resulting in a dark red-brown solution. A quantity of 1,2,3-trichloropropane (221 g, 1.50 moles) was then added to the dropping funnel. This content of the dropping funnel was then added to the stirred contents of the flask. The rate of addition was adjusted so as to maintain a vigorous, but controlled rate of reflux from the resulting exothermic reaction. It was noted that a salt precipitate had already begun to form at the completion of the addition of the contents of the dropping funnel. At the completion of the addition, additional anhydrous ethanol (188 g, 239 mL) was added and the reflux was maintained for several more hours to complete the reaction, during which time the formation of more salt precipitate was evident. The reaction mixture was then cooled to ambient temperature and filtered to remove solids. The solvent was removed by rotary evaporation at an absolute pressure of less than 1 torr at 65° C., whereupon a smaller additional quantity of solid precipitate appeared, which was subsequently removed from the resulting viscous, dark red liquid by decantation.

EXAMPLES 3 AND 4

The hydrocarbon core polysulfide silanes prepared in Examples 1 and 2 were used as the coupling agent to prepare a low rolling resistance tire tread formulation. The rubber composition used was the following, where the figures listed under the PHR heading indicate the mass of the corresponding ingredient used relative to 100 total mass units of polymer (in this case, SSBR and polybutadiene) used:

| PHR | Ingredient |
|---|---|
| 75 | SSBR (12% styrene, 46% vinyl, $T_g$: 42° C.) |
| 25 | cis-1,4-polybutadiene (98% Cis, $T_g$: 104° C.) |
| 80 | Silica (150–190 $m^2$/gm, ZEOSIL ™ 1165MP, Rhone-Poulenc) |
| 32.5 | Aromatic process oil (high viscosity, Sundex ™ 8125, Sun Co., Inc.) |
| 2.5 | Zinc oxide (KADOX ™ 720C, Zinc Corp) |
| 1 | Stearic acid (INDUSTRENE ™ , Crompton Corp., Greenwich, CT) |
| 2 | 6PPD antiozonant (SANTOFLEX ™ 6PPD, Flexsys) |
| 1.5 | Microcrystalline wax (M-4067, Schumann) |
| 3 | N330 carbon black (Engineered Carbons) |
| 1.4 | Sulfur (#104, Sunbelt) |
| 1.7 | CBS accelerator (SANTOCURE ™, Flexsys) |
| 2 | DPG accelerator (PERKACIT ™ DPG-C, Flexsys) |
| see Table I | Silane |

The hydrocarbon core polysulfide silanes prepared by the procedures described in Examples 1 and 2 were used to prepare the rubber compositions described in Examples 3 and 4. A control was run side by side with Examples 3 and 4 to provide a meaningful basis of comparison for the performance as a coupling agent in silica-filled rubber of the representative examples presented herein of the hydrocarbon core polysulfide silanes. The silane used in the control was the current industry standard coupling agent for rubber for silica-filled tire treads, the nominal bis(3-triethoxysilyl-1-propyl)tetrasulfide (TESPT). The rubber compounding formulations and procedures used in Examples 3 and 4 and in the control were identical with the exception of the silane used as the coupling agent. The silane loading levels used were also identical with respect to the loadings of silicon delivered. This necessitated the use of slightly different loading levels on an actual mass (i.e., weight) basis due to molecular weight differences among the silanes evaluated. The samples were prepared using a Model B BANBURY (Farrell Corp.) mixer with a 103 cu. in. (1690 cc) chamber volume. A rubber masterbatch was prepared in a two step procedure. The mixer was set at 120 rpm with the cooling water on full. The rubber polymers were added to the mixer while running and ram down mixed for 30 seconds. Approximately half of the silica (about 35–40 g), and all of the hydrocarbon core polysulfide silane (in an ethylvinyl acetate (EVA) bag) were added and ram down mixed for 30 seconds. The remaining silica and the oil (in an EVA bag) were then added and ram down mixed for 30 seconds. The mixer throat was dusted down three times and the mixture ram down mixed for 15 seconds each time. The mixing speed was increased to between about 160–240 rpm as required to raise the temperature of the rubber masterbatch to between about 160 and 165° C. in approximately 1 minute. The masterbatch was removed from the mixer and using this composition, a sheet was then formed on a roll mill set at about 50 to 60° C., and then allowed to cool to ambient temperature.

The masterbatch was then again added to the mixer with the mixer at 120 rpm and cooling water turned on full and ram down mixed for 30 seconds. The remainder of the ingredients were then added and ram down mixed for 30 seconds. The mixer throat was dusted down, and the mixer speed was increased to about 160–240 rpm in order to increase the temperature of the mix to about 160–165° C. in approximately 2 minutes. The rubber composition was mixed for 8 minutes with adjustments to the mixer speed in order to maintain the temperature between about 160–165° C. The composition was removed from the mixer and a sheet about 3 inch thick was formed on a 6×12 inch roll mill set at about 50 to 60° C. This sheet was then allowed to cool to ambient temperature.

The resulting rubber composition was subsequently mixed with the curatives on a 6 in.×13 in. (15 cm×33 cm) two roll mill that was heated to between 50 and 60° C. The sulfur and accelerators were then added to the composition and thoroughly mixed on the roll mill and allowed to form a sheet. The sheet was cooled to ambient conditions for 24 hours before it was cured.

The rheological properties of the rubber compound so prepared were measured on a Monsanto R-100 Oscillating Disk Rheometer and a Monsanto M1400 Mooney Viscometer. A Rheometrics ARES was used for dynamic mechanical analysis. The specimens for measuring the mechanical properties were cut from 6 mm plaques cured for 35 minutes at 160° C. or from 2 mm plaques cured for 25 minutes at 160° C.

The hydrocarbon core polysulfide silanes, whose preparation was described in Examples 1 and 2, were compounded into the tire tread formulation according to the above procedure. In Example 3, the hydrocarbon core polysulfide silane prepared in Example 1 was used, and in Example 4, the hydrocarbon core polysulfide silane prepared in Example 2 was used.

These examples were tested against a control sample which is nominally bis-(3-triethoxysilyl-1-propyl) tetrasulfide (TESPT), an industry standard coupling agent. Its actual composition is a mixture of polysulfides, with significant contributions from individual species containing chains of from 2 to 8 sulfur atoms. The compositions were tested using standard testing procedures. The results of the testing are summarized in Table 1 below.

TEST METHODS

1. Mooney Scorch
   ASTM D1646.
2. Mooney Viscosity
   ASTM D1646.
3. Oscillating Disc Rheometer (ODR
   ASTM D2084.
4. Physical Properties; Storage Modulus, Loss Modulus, Tensile & Elongation
   ASTM D412 and D224.
5. DIN Abrasion
   DIN Procedure 53516.
6. Heat Buildup
   ASTM D623. Heat build-up was measured at 100° C. using an 18.5% compression, 143 psi load and a 25 minute run. A sample which was at ambient conditions was placed in an oven that had been preheated to 100° C. The sample was conditioned at 100 C for 20 minutes and then given a 5 minute test run.
7. % Permanent Set
   ASTM D623.
8. Shore A Hardness
   ASTM D2240.

TABLE I

Properties and Processing Parameters

|  | Example 3 | | Example 4 | | Control | |
| --- | --- | --- | --- | --- | --- | --- |
| Silane: Type and Amount | Silane 1 | | Silane 2 | | TESPT | |
| Silane Loading (phr) | 9.5 | | 9.5 | | 7.0 | |
| Silane Si Loading, moles Si/100 g. rubber | 0.027 | | 0.027 | | 0.027 | |
| Elemental Sulfur in Curatives (phr) | 1.4 | — | 1.4 | — | 1.4 | — |
| Mooney Viscosity @ 100° C. (ML1 + 4) | 90 | 76 | 80 | 87 | 70 | 71 |
| Mooney Scorch @ 135° C., minutes | | | | | | |
| MS1 + $t_3$ | 5.0 | 3.7 | 4.2 | 3.5 | 6.6 | 6.6 |
| MS1 + $t_{18}$ | 7.3 | 8.3 | 6.3 | 6.8 | 9.4 | 13.5 |
| MS1 + | 49.8 | 57.5 | 44.6 | 52.7 | 32.8 | 37.3 |
| ODR @ 149° C., 1° Arc; 30 minutes | | | | | | |
| $M_L$, dN-m | 12.3 | 12.0 | 11.3 | 11.1 | 10.1 | 9.8 |
| $M_L$, lb-in | 10.9 | 10.6 | 10.0 | 9.8 | 8.9 | 8.7 |
| $M_H$, dN-m | 35.8 | 22.5 | 34.6 | 21.5 | 32.9 | 18.5 |
| $M_H$, lb-in | 31.7 | 19.9 | 30.6 | 19.0 | 29.1 | 16.4 |
| $t_{s1}$, minutes | 4.2 | 5.9 | 3.5 | 3.6 | 4.6 | 7.3 |
| $t_{90}$, minutes | 16.9 | 20.0 | 15.3 | 17.9 | 17.3 | 22.8 |
| Physical Properties; 90 minute cure @ 149° C. | | | | | | |
| Shore A Hardness | 60 | 51 | 59 | 51 | 60 | 48 |
| % Elongation | 325 | 518 | 344 | 528 | 379 | 587 |
| 25% Modulus, MPa | 0.93 | 0.63 | 0.96 | 0.63 | 0.84 | 0.57 |

TABLE I-continued

Properties and Processing Parameters

|  | Example 3 |  | Example 4 |  | Control |  |
|---|---|---|---|---|---|---|
| 25% Modulus, psi | 135 | 91 | 139 | 92 | 122 | 83 |
| 100% Modulus, MPa | 2.9 | 1.3 | 2.7 | 1.3 | 2.3 | 1.0 |
| 100% Modulus, psi | 421 | 195 | 398 | 186 | 327 | 150 |
| 200% Modulus, MPa | 9.9 | 3.3 | 8.9 | 2.9 | 7.0 | 2.1 |
| 200% Modulus, psi | 1437 | 484 | 1287 | 427 | 1017 | 301 |
| 300% Modulus, MPa | 19 | 7.0 | 18 | 5.8 | 15 | 3.9 |
| 300% Modulus, psi | 2809 | 1017 | 2554 | 847 | 2157 | 560 |
| Tensile Strength, MPa | 21 | 16.2 | 21 | 13.6 | 22 | 10.3 |
| Tensile Strength, psi | 3078 | 2348 | 3086 | 1976 | 3123 | 1500 |
| Modulus Ratio (300%/25% Mod.) | 20.8 | 11.2 | 18.4 | 9.2 | 17.7 | 6.7 |
| Reinforcement Index (300%/100% Mod.) | 6.7 | 5.2 | 6.4 | 4.6 | 6.6 | 3.7 |
| Low-Strain Dynamic Properties: Simple Shear @ 60° C. and 5.0 N Compressive Normal Force | | | | | | |
| $G'_{0\% \text{ strain}}$, MPa * | 2.12 | | 2.48 | | 2.45 | |
| delta $G' = G'_{0\% \text{ strain}} - G'_{10\% \text{ strain}}$, MPa * | 0.60 | | 0.83 | | 1.00 | |
| $G''_{max}$, MPa | 0.22 | | 0.28 | | 0.29 | |
| Maximum Tan Delta Value | 0.13 | | 0.15 | | 0.165 | |
| Heat Build-up, 100° C., 17.5% Compression, 990 Kpa (143 psi) static load, 25 minute run | | | | | | |
| Delta T, ° C. | 14 | | 15 | | 17 | |
| % Permanent Set | 4.5 | | 6.0 | | 6.5 | |

$G'_{0\% \text{ strain}}$ taken to mean the limiting value of G' as the strain approaches zero Table I above presents performance parameters of the hydrocarbon core polysulfide silanes of the present invention and of TESPT, the prior art silane which is the current industry standard. The levels of the dynamic properties at low strain of rubber compounded with Silane 1 are consistently and substantially below those of TESPT. These values lie at 0.60, 0.22, and 0.13 for delta G', $G''_{max}$, and the maximum tan delta value, respectively for Silane 1, whereas the corresponding values for TESPT are 1.00, 0.29, and 0.165, respectively. This trend is similar, although less dramatic, with Silane 2. The lower values for these parameters in Silanes 1 and 2 relative to TESPT are a clear indication to one skilled in the art that Silanes 1 and 2 do a better job of dispersing the filler than the industry standard.

The objects of the invention are achieved. The hydrocarbon core polysulfide silanes of the present invention provide multiple silyl groups without ether linkages to provide enhanced performance in filled elastomer compositions, rubber compositions, and use in tire compositions. The non-collinear structure of the hydrocarbon core polysulfide silanes provide enhanced dispersibility of the filler within an elastomer composition. Use of the hydrocarbon core polysulfide silanes of the present invention result in low rolling resistance tires having enhanced performance characteristics.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A polysulfide silane composition having the formula:

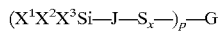

wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom from R, and G is a hydrocarbon fragment obtained by removal of a p quantity of hydrogen atoms from a hydrocarbon having from 1 to 30 carbon atoms.

2. The polysulfide silane composition of claim 1 wherein $X^1$, $X^2$ and $X^3$ are the same hydrolyzable functionalities.

3. The polysulfide silane composition of claim 1 wherein $X^1$, $X^2$ and $X^3$ are ethoxy.

4. The polysulfide silane composition of claim 1 wherein $X^1$, $X^2$ and $X^3$ are each different hydrolyzable functionalities.

5. The polysulfide silane composition of claim 1 wherein p is 3 to 6.

6. The polysulfide silane composition of claim 1 wherein x is 2 to 8.

7. The polysulfide silane composition of claim 1 wherein R is a hydrocarbon moiety selected from the group consisting of straight chain alkyl, alkenyl, aryl and aralkyl groups.

8. The polysulfide silane composition of claim 1 wherein J is selected from the group consisting of methylene, ethylene, propylene, isobutylene, and diradicals obtained by loss of hydrogen atoms at a 2,4 or 2,5 position of norbornane, an alpha position of 2-norbornylethane, a beta position of 2-norbornylethane, a 4 position of 2-norbornylethane, or a 5 position of 2-norbornylethane.

9. The polysulfide silane composition of claim 1 wherein p is 3 and G is glyceryl.

10. The polysulfide silane composition of claim 1 wherein p is 3 and G is a hydrocarbon fragment obtained by removal of 3 hydrogen atoms from 2-norbornylethane.

11. The polysulfide silane composition of claim 1 wherein p is 3 and G is a hydrocarbon fragment obtained by removal of 3 hydroxyl groups from a trimethylolalkane.

12. The polysulfide silane composition of claim 1 wherein p is 4 and G is pentaerythrityl.

13. The polysulfide silane composition of claim 1 wherein p is 4 and G is a hydrocarbon fragment obtained by removal of 4 hydrogen atoms from 2-norbornylethane.

14. The polysulfide silane composition of claim 1 wherein p is greater than 4 and G is a hydrocarbon fragment obtained by removal of more than 4 hydrogen atoms from cyclododecane, triethylcyclohexane, 2,6-dimethyloctane, or squalane.

15. The polysulfide silane composition of claim 1 wherein G contains a tertiary amine functionality.

16. The polysulfide silane composition of claim 1 wherein G contains a cyano functionality.

17. A polysulfide silane composition comprising one or more isomers of tetrakis-1,3,4,5-(3-triethoxysilyl-1-propyltetrathio)neopentane.

18. A polysulfide silane composition comprising one or more isomers of tris-1,2,3-(3-triethoxysilyl-1-propyltetrathio)propane.

19. A process of making a hydrocarbon core polysulfide silane having the formula

$(X^1X^2X^3Si-J-S_x-)_p-G$ wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom from R, and G is a hydrocarbon fragment obtained by removal of a p quantity of hydrogen atoms from a hydrocarbon having from 1 to 30 carbon atoms, comprising the steps of:
providing a mercaptan;
deprotonating the mercaptan;
providing a source of elemental sulfur;
forming a reactive sulfur anion by reacting the deprotonated mercaptan with the elemental sulfur; and
coupling the reactive sulfur anion with a carbon containing substrate.

20. The process of claim 19 wherein the step of providing the mercaptan comprises providing a mercaptan having a formula $X^1X^2X^3Si-J-SH$.

21. The process of claim 20 wherein the step of providing the mercaptan comprises providing a mercaptan selected from the group consisting of 3-mercapto-1-propyltriethoxysilane and 3-mercapto-1-propylmethyldiethoxysilane.

22. The process of claim 19 wherein the step of providing the mercaptan comprises providing a mercaptan having a formula $(HS_x-)_pG$.

23. The process of claim 22 wherein the step of providing the mercaptan comprises providing a mercaptan selected from the group consisting of 2,2-bis(mercaptomethyl)-1,3-dimercaptopropane and 1,2,3-trimercaptopropane.

24. The process of claim 19 wherein the step of deprotonating the mercaptan comprises deprotonating the mercaptan with a Brönsted base using p equivalents of the base for each mole of mercaptan.

25. The process of claim 19 wherein the step of deprotonating the mercaptan comprises deprotonating the mercaptan with a non-ionic Brönsted base.

26. The process of claim 19 wherein the step of forming the reactive sulfur anion is complete prior to introduction of the carbon containing substrate.

27. An elastomeric composition comprising
at least one hydrocarbon core polysulfide silane having the formula

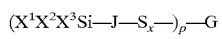

$(X^1X^2X^3Si-J-S_x-)_p-G$ wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or hydrogen, J is a hydrocarbon fragment obtained by removal of one hydrogen atom from R, and G is a hydrocarbon fragment obtained by removal of a p quantity of hydrogen atoms from a hydrocarbon having from 1 to 30 carbon atoms;
an unsaturated organic polymer; and
a filler.

28. The elastomeric composition of claim 27 wherein the at least one hydrocarbon core polysulfide silane is one or more isomers of tetrakis-1,3,4,5-(3-triethoxysilyl-1-propyltetrathio)neopentane.

29. The elastomeric composition of claim 27 wherein the at least one hydrocarbon core polysulfide silane is one or more isomers of tris-1,2,3-(3-triethoxysilyl-1-propyltetrathio)propane.

30. The elastomeric composition of claim 27 wherein the at least one hydrocarbon core polysulfide silane is present in an amount of about 0.05 to about 25 phr.

31. The elastomeric composition of claim 27 wherein the filler is present in an amount of about 1 to about 85 wt. % of carbon black based on a total weight of the filler and the at least one hydrocarbon core polysulfide silane is present in an amount of about 0.1 to about 20 wt. % of the hydrocarbon core polysulfide silane based on a total weight of the filler.

32. A process of making a rubber composition comprising the steps of
providing at least one isomer of a hydrocarbon core polysulfide silane having the formula

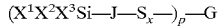

$(X^1X^2X^3Si-J-S_x-)_p-G$ wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom from R, and G is a hydrocarbon fragment obtained by removal of a p quantity of hydrogen atoms from a hydrocarbon having from 1 to 30 carbon atoms;
providing an organic polymer;
providing a filler;
thermomechanically mixing the organic polymer, filler and hydrocarbon core polysulfide silane to form a rubber mixture;
curing the rubber mixture to form a rubber composition having enhanced dispersion of the filler.

33. The process of claim 32 wherein during the step of providing the filler, the filler has been pretreated with the hydrocarbon core polysulfide silane.

34. The process of claim 32 further including the step of adding curing agents to the rubber mixture in another thermomechanical mixing stage before curing the rubber mixture.

35. The process of claim 32 wherein the hydrocarbon core polysulfide silane is one or more isomers of tetrakis-1,3,4,5-(3-triethoxysilyl-1-propyltetrathio)neopentane.

36. The process of claim 32 wherein the hydrocarbon core polysulfide silane is one or more isomers of tris-1,2,3-(3-triethoxysilyl-1-propyltetrathio)propane.

37. A filler for dispersion in elastomeric compositions comprising:

mineral particulates; and at least one hydrocarbon core polysulfide silane having the formula:

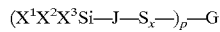

wherein p is 3 to 12, x is 2 to 20, $X^1$ is a hydrolyzable functionality selected from the group consisting of —Cl, —Br, —OH, —O—N=C(R)$_2$, —OR, and RC(=O)O—, in which R is a hydrocarbon fragment obtained by removing one hydrogen atom from a hydrocarbon having 1 to 20 carbon atoms, $X^2$ and $X^3$ are $X^1$, R or H, J is a hydrocarbon fragment obtained by removal of one hydrogen atom from R, and G is a hydrocarbon fragment obtained by removal of a p quantity of hydrogen atoms from a hydrocarbon having from 1 to 30 carbon atoms.

38. The filler of claim 37 wherein the mineral particulates are siliceous particulates.

39. The filler of claim 37 further comprising carbon black.

40. The filler of claim 37 wherein the at least one hydrocarbon core polysulfide silane is one or more isomers of tetrakis-1,3,4,5-(3-triethoxysilyl-1-propyltetrathio) neopentane.

41. The filler of claim 37 wherein the at least one hydrocarbon core polysulfide silane is one or more isomers of tris-1,2,3-(3-triethoxysilyl-1-propyltetrathio)propane.

* * * * *